(12) United States Patent
Sellberg et al.

(10) Patent No.: US 12,364,567 B2
(45) Date of Patent: *Jul. 22, 2025

(54) HEALTHCARE MONITORING METHOD AND SYSTEM FOR SECURE COMMUNICATION OF PATIENT DATA

(71) Applicant: ADDI MEDICAL AB, Danderyd (SE)

(72) Inventors: Nina Sellberg, Stockholm (SE); Casper Winsnes, Saltsjö-Boo (SE); Fredrik Henriques, Stockholm (SE); Björn Strihagen, Täby (SE)

(73) Assignee: ADDI MEDICAL AB, Danderyd (SE)

( * ) Notice: Subject to any disclaimer, the term of this patent is extended or adjusted under 35 U.S.C. 154(b) by 912 days.

This patent is subject to a terminal disclaimer.

(21) Appl. No.: 17/533,645

(22) Filed: Nov. 23, 2021

(65) Prior Publication Data

US 2022/0117692 A1   Apr. 21, 2022

Related U.S. Application Data

(63) Continuation-in-part of application No. 16/330,500, filed on Mar. 5, 2019, now Pat. No. 11,188,676.

(51) Int. Cl.
*A61B 90/25* (2016.01)
*A61B 90/50* (2016.01)
*B25J 15/00* (2006.01)
*B25J 19/00* (2006.01)

(52) U.S. Cl.
CPC .............. *A61B 90/25* (2016.02); *A61B 90/50* (2016.02); *B25J 15/0019* (2013.01); *B25J 19/0016* (2013.01)

(58) Field of Classification Search
CPC .. G06F 21/6245; G06F 21/6254; G06F 21/62; H04L 9/3226; H04L 9/0819; H04L 2209/88; H04L 9/08; G16H 10/60; G16H 10/00
See application file for complete search history.

(56) References Cited

U.S. PATENT DOCUMENTS

2005/0162623 A1   7/2005  Landi et al.
2008/0304663 A1   12/2008 Canard

FOREIGN PATENT DOCUMENTS

WO        2012015645 A2    2/2012

*Primary Examiner* — Pei Yong Weng
(74) *Attorney, Agent, or Firm* — Renner, Otto, Boisselle & Sklar, LLP

(57) ABSTRACT

There are provided methods in a healthcare monitoring system for anonymous communication of patient data associated with a patient between at least one electronic user device, using a respective client application implemented in the electronic user device, and a host server, using a host application implemented in the host server, via a wireless network. Embodiments of the method further enables identification of the patient associated with the anonymous patient data in a secure manner. There is further provided corresponding systems, computer programs and non-volatile data carriers containing the computer programs.

21 Claims, 9 Drawing Sheets

Process for Secure Communication of Digital Information – Between a Client Application and a Host Application

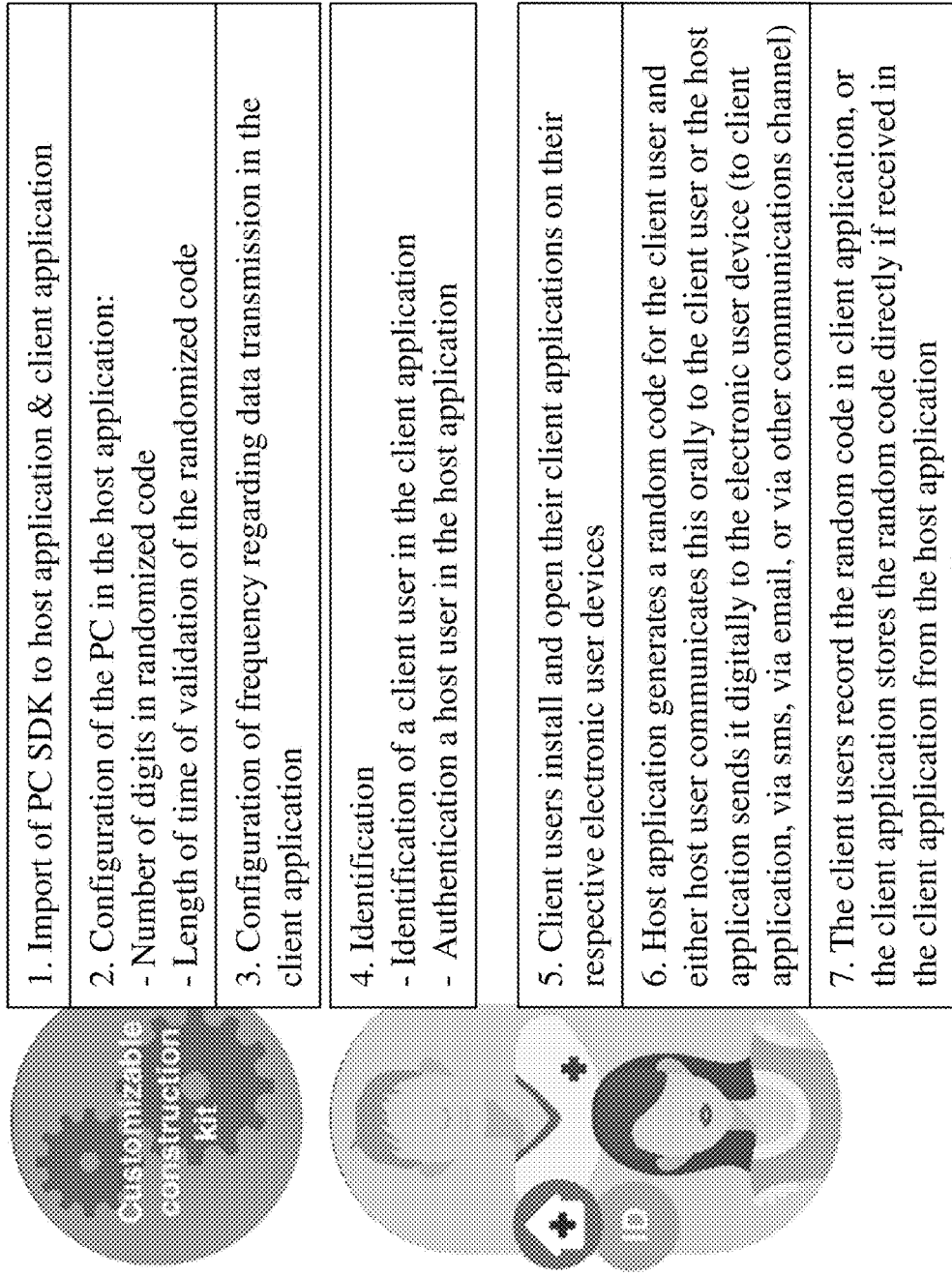

| |
|---|
| 1. Import of PC SDK to host application & client application |
| 2. Configuration of the PC in the host application:<br>- Number of digits in randomized code<br>- Length of time of validation of the randomized code |
| 3. Configuration of frequency regarding data transmission in the client application |
| 4. Identification<br>- Identification of a client user in the client application<br>- Authentication a host user in the host application |
| 5. Client users install and open their client applications on their respective electronic user devices |
| 6. Host application generates a random code for the client user and either host user communicates this orally to the client user or the host application sends it digitally to the electronic user device (to client application, via sms, via email, or via other communications channel) |
| 7. The client users record the random code in client application, or the client application stores the random code directly if received in the client application from the host application |

FIG. 4

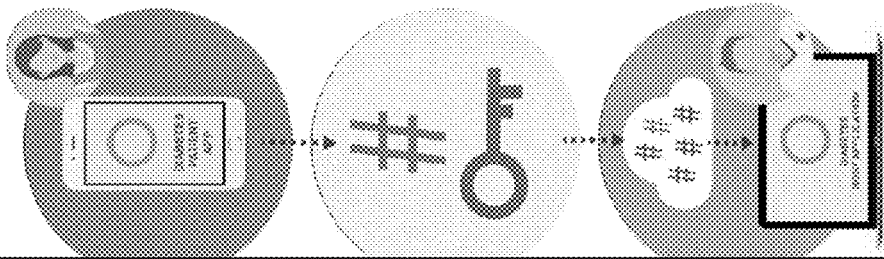

8. Pairing between the host application and patient app is as follows:
- When the random code was developed in host application an ID was created for the client user (this ID is not based on any personal identification and can not be linked to an individual)
- When initiating a pairing between the host application and client application by recording the random code in the client application, the PC in the host application creates an access key that is sent to the client application
- The PC in the host application stores a hash of the access key that has been sent to the client application
- Each time a transfer of data is sent from the client application to the host application, the access key is also accompanied this transfer
- PC in the host application runs the access key through a mathematical function that generates the hash linked to this access key
- The generated hash is thereafter matched against all stored hashes in the host application to look up the client user that the data belongs to 9. Anonymized data is sent continuously and interactively hereafter between the client application and the host application (sent from client application to host application or requested and retrieved from host application to client application) using the same access key and turned towards the same hash on each occasion 10. The pairing between the host application and client application is terminated when either:
- The client user deletes the client application from his/her electronic user device
- The host user deletes the client user in the host application by deleting the hash that is related to the client user FIG. 4
(continuation)

HEALTHCARE MONITORING METHOD AND SYSTEM FOR SECURE COMMUNICATION OF PATIENT DATA

RELATED APPLICATIONS

This application is a continuation in part of the U.S. patent application Ser. No. 16/330,500 filed on Mar. 5, 2019 as the national phase entry of International Application No. PCT/EP2017/072237 filed on Sep. 5, 2017, which claims the benefit of U.S. Provisional Application No. 62/383,716 filed Sep. 6, 2016, all of which are hereby incorporated by reference.

TECHNICAL FIELD

The present invention relates generally to solutions for enabling secure communication of patient data.

More particularly, the invention relates to a method for enabling secure communication of patient data according to the preamble of claim 1, and corresponding system. The invention also relates to a computer program and a non-volatile data carrier.

BACKGROUND

Healthcare is used as an example of an owner of a host application in the text below. The owner of the host application could however be any party or organization that could have an interested in an individual's or patient's registered health data. The health data is typically represented as quantitative data such as number of steps, weight, electrocardiography measures, spirometer measures, blood pressure, degree of patient's perceptive of pain etc. or qualitative data which is the individual's perception written in free text format. Patient data as described herein may besides health data include e.g., a medical diagnosis, test results, or other sensitive medical data concerning a patient.

The party and/or organisation having interest in the individual's registered quantitative or qualitative data described could be public or private healthcare, academic research projects, industry research projects, public/private registries, qualitative registries, bio banks, health authorities etc. The data might also be retrieved on a consent basis for follow-up of the sale of consumer goods for functionality or quality checks and for customer satisfaction screening or for direct marketing purposes. Another party having interest in the individual's registered quantitative or qualitative data could be the pharmaceutical industry.

Transfer of data means that information is sent via a message between the app in the client's or patient's device and the host application implemented on a healthcare server, also referred to as the host server or simply the host.

A Software Development Kit ("SDK") is a component/set of software development tools that allows the creation of applications for a certain software package, software framework, patient application, electronic health record, research system or other applications and systems.

SUMMARY

The present invention enables secure communication of sensitive patient data between a host application and a client application, by connecting the host application the client application, which is an application implemented in an electronic user device of a client user, e.g., but not limited to a patient. The client device may be holding patient registered or patient generated information, which is typically the case if the client user is a patient registering personal patient data as described in some embodiments herein.

The host application and the client application have been paired through an authorization process done using strong authorization, either during a meeting in person or using the host application and/or the client application. The system, or platform, also referred to as the "patient connector" (PC) enabling the pairing and thereafter secure communication of patient data, in manners described herein, is distributed as a software development kit (SDK) that is imported into the host application and the client application. The PC pairs the host application with the patient app in a secure and accurate way. The PC provides transferring of anonymous patient information between the client application in the client device and the host application in the host server.

Different aspects and embodiments of the present invention are provided in the appended claims. These and additional embodiment, along with advantages, are further described in the detailed description in connection with the figures.

DESCRIPTION OF THE FIGURES

The invention will now be described in more detail with reference to the appended drawings, wherein:

FIG. 4 shows a flow diagram illustrating a process for secure communication of digital information, comprising steps according to one or more method embodiments of the invention;

Figure 1:
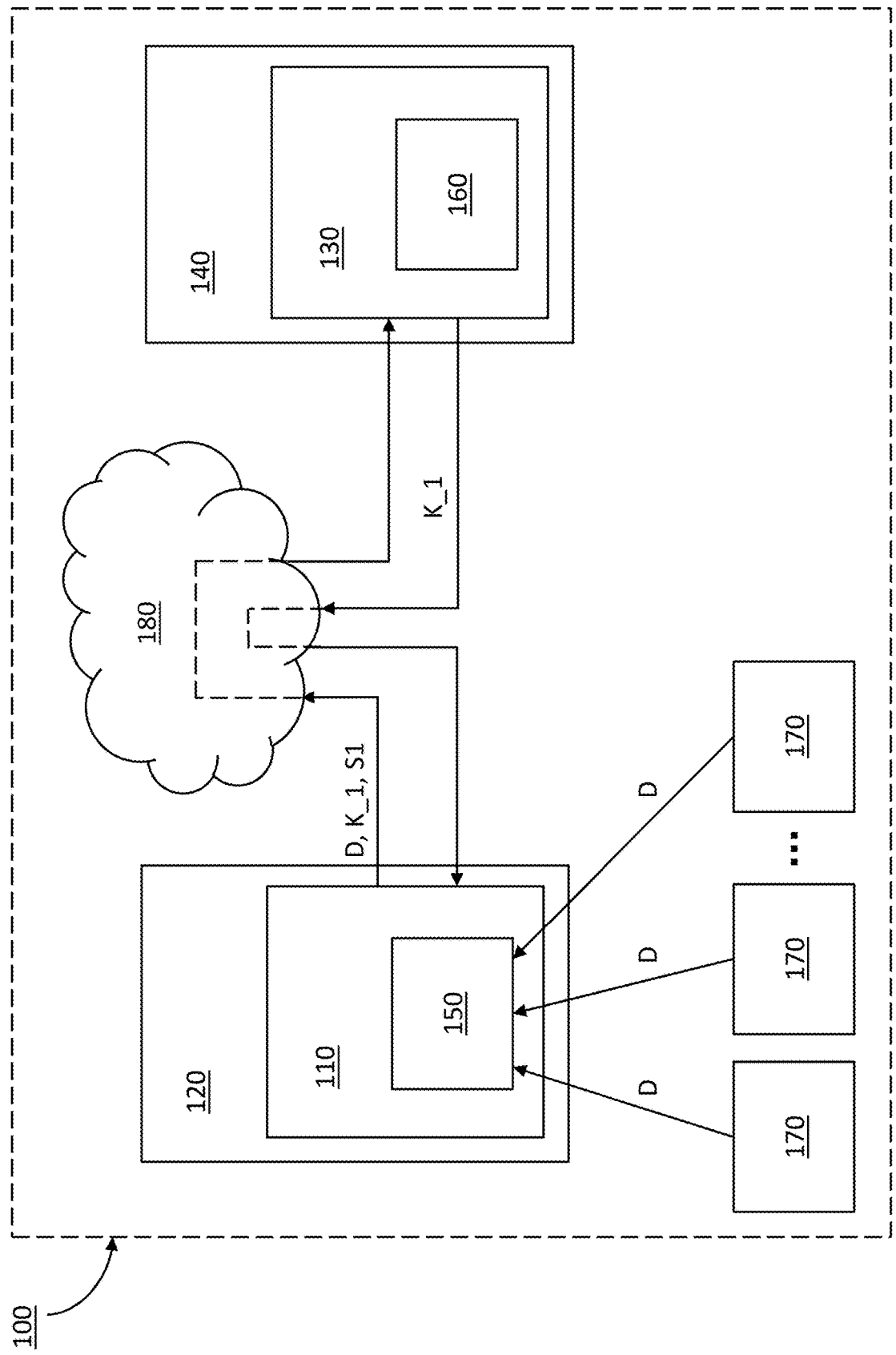
FIG. 1 shows an overview of a system according to one or more embodiments of the invention.

All the figures are schematic, not necessarily to scale, and generally only show parts which are necessary in order to elucidate the respective embodiments, whereas other parts may be omitted or merely suggested. Any reference number appearing in multiple drawings refers to the same object or feature throughout the drawings, unless otherwise indicated.

DESCRIPTION OF THE INVENTION

The subject invention provides secure communication of patient data by transferring only information that does not include personal or individual identification information so as to keep the identity of the information provider(s) confidential during the transfer of information. The client application and the host application of the present invention are paired through generating a unique access key, e.g., a randomized generated code that is unique for the client user, i.e., the user of the electronic user device. The client user is in some cases the subject patient, but may in other case be a healthcare professional, a representative of an academic faculty, or another party having a legitimate interest in patient data and therefore being entitled access to some patient data, depending on the access rules set in the system. The generated unique access key does not comprise any information that can be linked to, or used to derive, the identity of the client user. For example, in the case where a randomized code is generated, the randomized code is transferred into an ID, or access key, in the client application that is also known to the host application. The ID, or access key, may thereafter be during transfer of patient data or request for transfer of patient data be matched with a stored hash of the original unique access key in the host application to identify the client user using the electronic client device and/or the patient associated with the patient data subject to the transfer or request for transfer.

In other words, embodiments presented herein enable secure communication of confidential and sensitive patient data, even via open, wireless networks such as the Internet, because the patient data is completely anonymous during the transfer from the client application to the host application, or vice versa. This is essential because there are strict regulations controlling handling of sensitive patient data that need to be fulfilled. For instance, embodiments presented herein aim at fulfilling the EU General Data Protection Regulation (GDPR).

In addition to this, embodiments presented herein further enable the host application, e.g., the application of a healthcare provider, care giver or other central actor being the owner of the host server to accurately associate patient data with the correct patient's identity after the patient data has been received from the patient application or before it is transferred to a client application in response to a request to receive patient data. This is also essential, as e.g., medical data sent by a patient to a host server is useless to the healthcare provider, caregiver, or other actor, if it cannot be established without a doubt with which patient the received patient data is associated. Not to mention that if it cannot be established without a doubt with which patient the received patient data is associated, patient security would be jeopardized due to risk of providing the wrong treatment to the wrong patient, or not providing treatment to a patient in need of it, e.g.

The invention provides a solution to the technical problem of securely transferring sensitive information over the internet or through other information networks.

The subject invention realizes the solution by, in one aspect wherein the client user is the patient associated with the patient data to be transferred, providing means and methods of sending such information unidentified and without personal identity information and pairing the unidentified information at the reception by the host with the identity information in the ID/access key. There was prior to the invention no solution to the challenge of sending unidentified patient data over the Internet and still be able to connect securely patient registered data in a client application to a host application, e.g., a health care decision support system, electronic healthcare record, or a research institution's information system or any other health or biotech related registry. Within the context of the present disclosure, patient registered data may be replaced with, or complemented by, patient generated data, without any modifications of the method and system embodiments being necessary. Current host systems are unable to tell with acceptable certainty what information belongs to which patient without accommodating patient identity information during the transfer of information. For applications where patients are transferring patient registered data to a health care provider for diagnosing or health care follow-up there is a need of un-identification, security and accuracy mechanisms when transferring data. The suggested invention resolves this problem by pairing the client application and the host application during a meeting in person between the patient and for instance a medical professional from healthcare. Alternatively, the meeting could be with a person conducting a pharmaceutical research project. In relation to this meeting the patient has securely identified herself at the registration desk at a department in a hospital and the medical professional has identified herself, with so called strong authentication, when logging into the host application. The procedures of identification and/or authentication meet required degrees of security and accuracy.

Alternatively, or additionally, the patient may in this aspect identify herself, using so called strong authentication, when logging into the client application or using another system provided by the medical professional from healthcare. Also in this case, the procedures of identification and/or authentication meet required degrees of security and accuracy.

Furthermore, in connection with performing the pairing of applications, the patient knowingly consents to the host application, and in turn the host (medical staff, caregiver or other actor as described herein), having access to the patient data that is anonymously communicated from the client application to the host application, and further having access to information uniquely identifying the patient associated with the patient data. According to embodiments described herein in connection with the figures, each time patient data is to be sent from the client application and also each time identification is to be performed in the host application, a check is performed to determine whether a pairing exists between the host application and the client application. In other words, the patient consent is checked every time. If the patient should for some reason no longer consent to sharing her patient data and identification data, the patient may delete the client application from her smartphone or other user device where the client application has been installed. Thereby, when the next check is performed, in step 240 or 280 in connection with FIG. 2, no pairing is found and the method ends. Thereby, a required degree of security is obtained to e.g., fulfill GDPR and other relevant legal regulations.

As mentioned herein, transfer of data in the context of the present invention means that information is sent via a message between the client application and the host application. The message may be in the form of an email, a text message (e.g., sms), a multimedia message (e.g., mms), a message in any other form sent over a communications platform such as e.g., a social media platform, or any other suitable digital message type for conveying information that is presently known in the art or that is developed in the future. The claimed solution is thereby independent of the communications platform or digital communication type used.

In any of the embodiments herein, the host application in the host, e.g., a server, may be the sender or the receiver depending on the direction of communication of patient data D between the host and client. Similarly, the client application in the digital user device, also referred to as the client, may be the sender or the receiver. In some cases, the client application or host application may be both sender and receiver of patient data.

System Architecture

A system 100 according to different embodiments will now be described in connection with FIGS. 1, 5 and 6.

In any of these embodiments, the client user may be the patient, or it may be a healthcare professional or any other person who has legitimate access to patient data associated with the patient and who wants to send this patient data to the host server using the secure, anonymous, communication solutions described herein.

If the client user is the patient, the identification of the client user is an identification of the patient associated with the patient data. This is the case in the first embodiment described below in connection with FIG. 1.

In FIG. 1, embodiments of a healthcare monitoring system 100 for anonymous communication of patient data D, associated with a patient P, from an electronic user device to a host server, via a wireless network, and identification of the patient P associated with the patient data D after the patient data D is received in the host server, are shown. This aspect is applicable when at least one electronic user device and corresponding client application functions as the sender(s) of patient data, and the host server and host application functions as the receiver.

Figure 6:
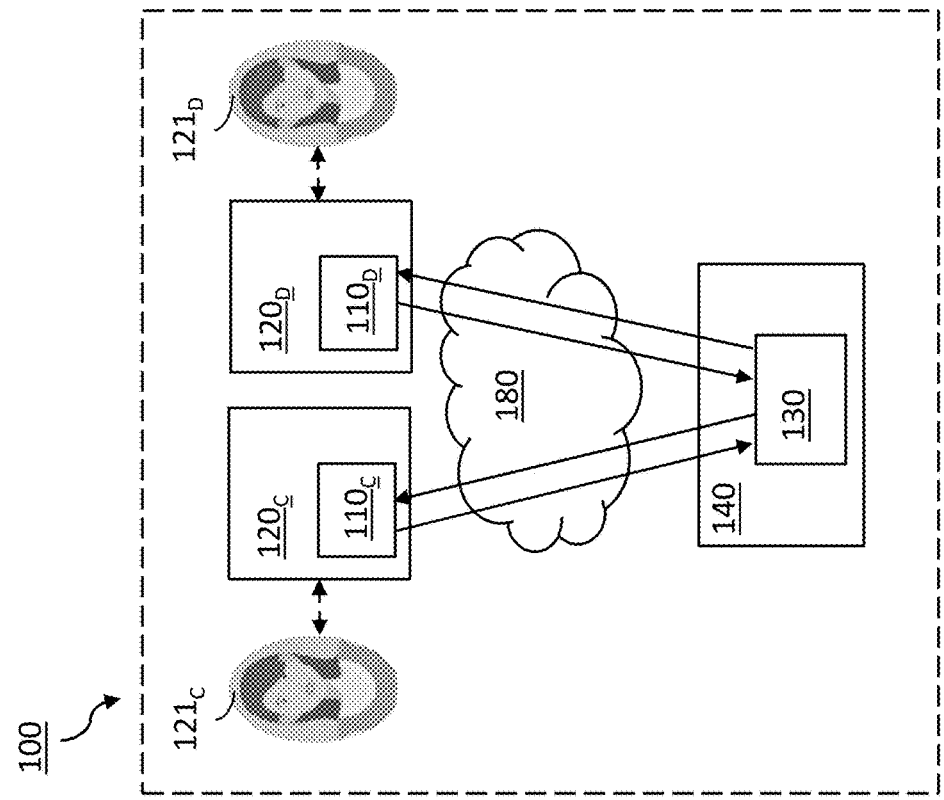
FIG. 6 shows an overview of a system according to one or more embodiments of the invention.
Figure 5:
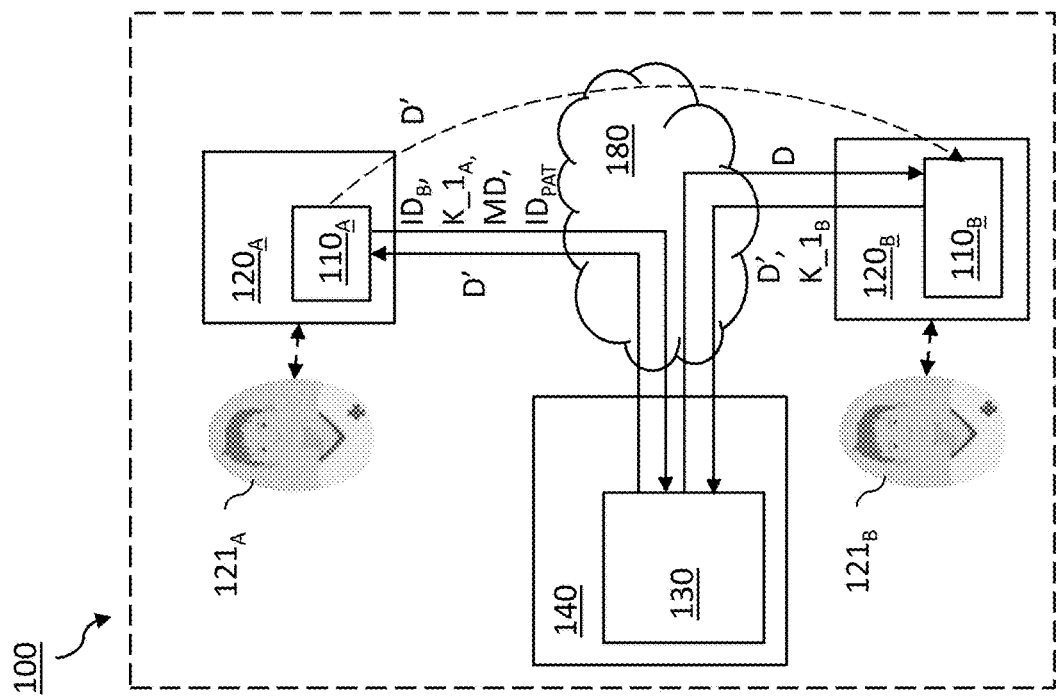
FIG. 5 shows an overview of a system according to one or more embodiments of the invention.

As can be seen from the arrows between the client applications and the host application in FIGS. 1, 5 and 6, communication of data is enabled in both directions.

According to one or more embodiments, the healthcare monitoring system 100 comprises an electronic user device 120, which comprises a client application 110; and a host server 140, which comprises a host application 130. The client application 110 may be referred to as a patient application in cases wherein the client user is a patient. However, the client user may be any actor communicating patient information via the system using an electronic user device 120. The client application 110 is configured to communicate with the host application 130 via a wireless network 180. The system 100 further comprises a memory 150 accessible by the client application 110 and a memory 160 accessible by the host application 130. In one or more embodiment, the system 100 is configured to pair the client application 110 and the host application 130. This is achieved by the host application being configured to i) generate a unique access key K for the client user, wherein the unique access key K is unrelated to any information identifying the client user, wherein the unique access key K comprises a first part K_1 and a second part K_2; ii) store the second part K_2 of the unique access key K in the memory 160 accessible by the host application 130, wherein the second part K_2 is stored in association with information identifying the client user; and iii) send the first part K_1 of the unique access key K to the client application 110. The client application 110 is configured to receive the first part K_1 of the unique access key K from the host application 130 and store the received first part K_1 of the unique access key K in the memory 150 accessible by the client application 110.

The client application 110 is further configured to send patient data D and the first part of the access key K_1 to the host application 130. In some embodiments, the client application 110 may be configured to receive patient data D from at least one patient data registering device 170. Alternatively, or additionally, the client application 110 may be configured to generate, receive, or retrieve patient data D in any other suitable manner. In embodiments wherein the client application 110 is configured to receive patient data D from at least one patient data registering device 170, it may further be configured to in response to receiving patient data D send the patient data D and the first part of the access key K_1 to the host application 130 in response to receiving the patient data D.

The host application 130 is further configured to: i) receive patient data D and the first part of the access key K_1 from the client application 100; and, if the client user is the patient, ii) identify the patient P associated with the received patient data D, based on the received second part K_2 of the access key K. Thereby, the patient data D is anonymous and secure when it is sent via the wireless network from the client application 110 to the host application 130, but is uniquely identified as being associated with the patient P after it is received in the host application.

If the client user is not the patient, the client application is in the case of sending patient data to the host application configured to also send, together with the patient data, anonymous information that the host application can use for identifying the patient once the patient data has been received in the host application. This is the case in the second embodiment described below in connection with FIG. 1.

The anonymous information may e.g., the first part of a unique access key associated with the patient, previously generated by pairing a client application implemented in an electronic user device of the patient with the host application, in any manner described herein. The anonymous information that the host application can use for identifying the patient may, previous to sending the patient data, have been retrieved by the client application sending information identifying the patient to the host application and retrieving in response the anonymous information, e.g., the first part of a unique access key associated with the patient, e.g., as described in steps 715-740 in connection with FIG. 7. Thereby, the anonymous information can be used in further sending of data or requesting of data related to at least one patient, even if the client user is not the patient.

In the second embodiment of FIG. 1, there is provided a healthcare monitoring system 100 for anonymous communication of patient data associated with a patient from an electronic user device 120 to a host server 140, via a wireless network 180, and identification of the patient associated with the patient data after the patient data is received in the host server, wherein the electronic user device comprises a client application 110; the host server comprises a host application 130; the client application is configured to communicate with the host application via the wireless network; and the system further comprises a memory 150 accessible by the client application, and a memory 160 accessible by the host application. The system is configured to pair the client application and the host application, by the host application being configured to:

generate a unique access key for the client user, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client;

store the second part of the unique access key in the memory accessible by the host application, wherein the second part is stored in association with information identifying the client user; and
send the first part of the unique access key to the client application;
and the client application being configured to:
store the received first part of the unique access key in the memory accessible by the client application;

The client application is further configured to send information identifying the patient and the first part of the access key from the client application to the host application. The host application is in turn configured to identify the client user associated with the unique access key, by: generating a second part of the access key, based on the received first part of the access key associated with the client user, if this has been sent, or otherwise using the first part of the access key generated through pairing of the client application of the client user and the host application; comparing the generated second part of the access key to one or more second parts of access keys stored in the memory accessible to the host application to find a matching second part, wherein the stored one or more second parts of access keys have been generated during pairing of the host application with one or more client applications; and if a matching second part of an access key is found, identifying the client user as the client user associated with the matching second part stored in the memory.

In response to identifying the client user the host application is further configured to identify the patient by mapping the received information identifying the patient to a list of patient identities stored in the memory of the host application, and send an anonymous personal ID associated with the identified patient to the client application.

Figure 7:
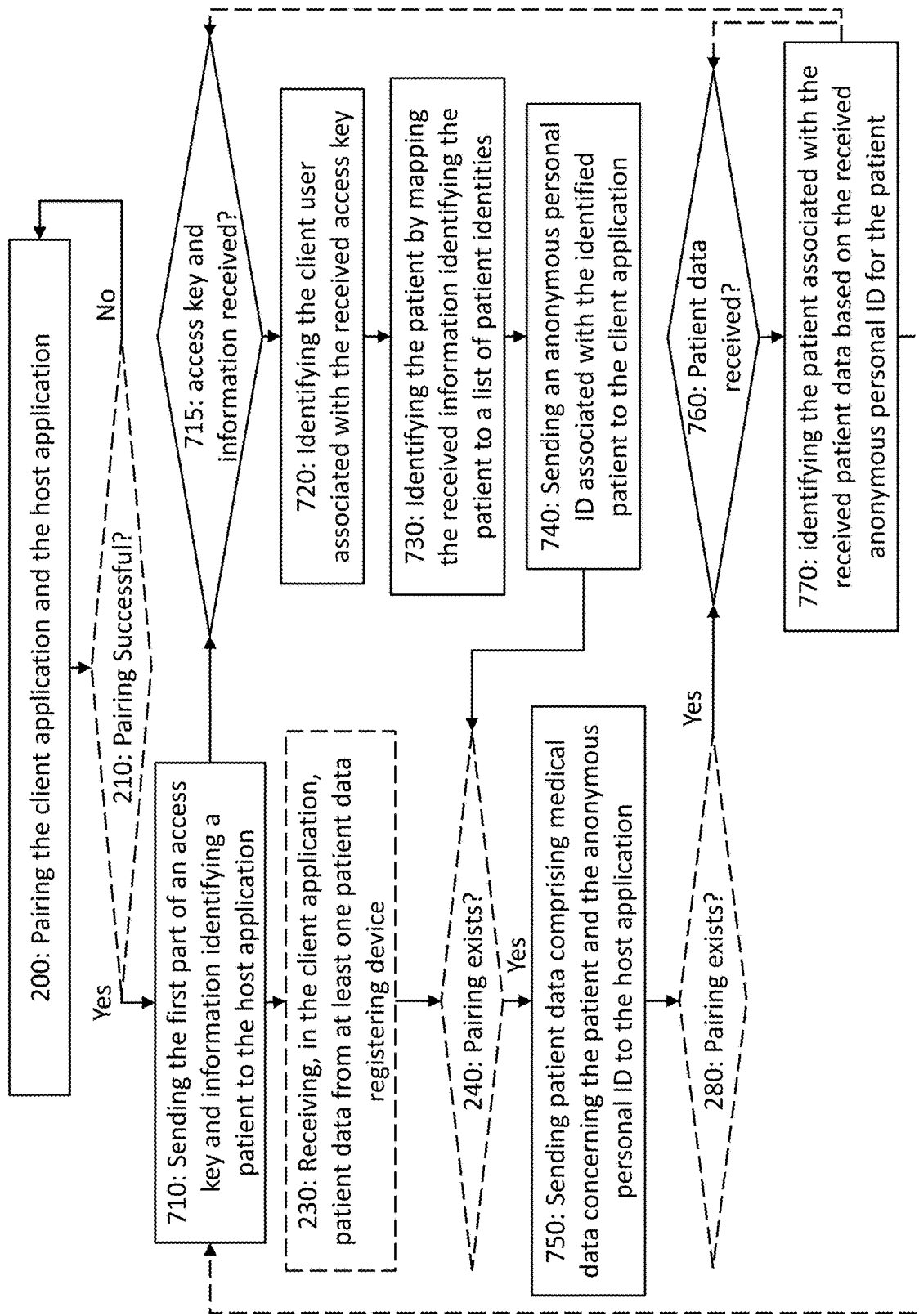
FIG. 7 shows a flow diagram illustrating a process for secure communication of digital information, comprising steps according to one or more method embodiments of the invention.

The anonymous personal ID for at least one patient may be retrieved from the host application by sending from the client application to the host application patient identity information for the at least one patient, mapping patient identity information for each of the at least one patient to a list of patient identities stored in the memory of the host server, and receiving in response, in the host application, a corresponding stored personal ID for each of the at least one patient, wherein the personal ID cannot be linked to the patient's, or individual's, identity, as described herein in connection with FIG. 7.

For ease of understanding, the embodiments herein are typically described as relating to one-way or two-way communication of patient data relating to one patient. Of course, all embodiments are equally applicable for communication of patient data for at least one patient, including patient data for two or more patients or even groups of patients, wherein an anonymous personal ID may be retrieved by mapping, or generated, for each of the at least one patient based on the respective received information identifying each patient.

The client application is further configured to send patient data from the client application to the host application, wherein the patient data comprises medical data concerning the patient and the anonymous personal ID for the patient, wherein neither the patient data nor the personal ID for the patient comprise any information identifying the patient.

The host application is further configured to receive the patient data and the anonymous personal ID for the patient identify the patient associated with the received patient data based on the received anonymous personal ID for the patient.

The host application 130 may in any of the first and second embodiment be configured to authenticate a caregiver, healthcare professional, or other entitled actor working for the owner of the host server 140, as an authorized user of the host application 130, using strong authentication, prior to the pairing of the client application 110 and the host application 130.

In any of the first and second embodiment, the client application 110 may be configured to authenticate a client user, e.g., but not limited to the patient P, as an authorized user of the client application 110, using strong authentication, prior to the pairing of the client application 110 and the host application 130.

In some embodiments wherein the client user is the patient P and patient data is securely communicated from the client application 100 to the host application 130, the host application 130 is configured to identify the patient P associated with the received patient data D, based on the second part $K\_2$ of the access key K, by: i) generating a second part $K\_2$ of the access key K, based on the received first part $K\_1$ of the access key K; ii) comparing the generated second part $K\_2$ of the access key K to one or more second parts of access keys stored in the memory 160 accessible to the host application 130 to find a matching second part, wherein the stored one or more second parts of access keys have been generated during pairing of the host application 150 with one or more client applications 110; and iii) if a matching second part of an access key is found, identifying the patient P as the client user associated with the matching second part stored in the memory 160.

In any of the first and second embodiment, generating a unique access key K for the client user, e.g. being the patient P, may be enabled by the host application 130 being configured to generate a randomized numeric code C that is unrelated to any information identifying the client user; the client application 110 being configured to receive the randomized numeric code C from the host application 130 and send a message in the form of a control signal S1 to the host application 130 in response to receiving the unique access key K; and the host application 130 being configured to receive the control signal S1 from the client application 110 and generate the unique access key K in response to receiving the control signal S1.

The healthcare monitoring system 100 in any of the first and second embodiment comprises or is connected to a memory 150 accessible to the patient application 110. The healthcare monitoring system 100 further comprises or is connected to a memory 160 accessible to the host application 130. In FIG. 1, memory 150 is illustrated as being part of the patient application 110 and memory 160 is illustrated as being part of the host application 130. However, the memory 150 may be integrated in, connected to, or communicatively coupled to the patient application 110, and the memory 160 may be integrated in, connected to, or communicatively coupled to the host application 130.

In some embodiments, for example as described above in connection with FIG. 1, at least one electronic user device and corresponding client application functions as the sender(s) of patient data, and the host server and host application functions as the receiver of the same. In other embodiments, at least one electronic user device and corresponding client application functions as the receiver(s) of patient data, and the host server and host application functions as the sender of the same. In some embodiments, each of the at least one electronic user device and corresponding client application and the host server and host application functions as both a sender(s) of patient data, and a receiver of patient data. Example of different embodiments with different communication manners are described further in connection with FIGS. 5 and 6 and the corresponding methods in FIGS. 7 and 8.

As an example, there may be a need for a first healthcare professional to obtain a second opinion from a second healthcare professional who is not at the same location as the first healthcare professional. In this case, the first healthcare professional would benefit from sending patient data to the second healthcare professional via secure communication means. The healthcare professionals are not allowed to send emails, sms, messages via unsecure communications platforms etc., containing data identifying the patient such as e.g., name or social security number in connection with the patient data D. However, using the present invention the healthcare professionals are enabled to send the patient data D, as long as the first and second healthcare professionals are communication via a respective client application that has been paired to the same host application. A system 100 wherein this communication is enabled is schematically illustrated in FIG. 5.

In FIG. 5, a client user $121_A$, who may in this non-limiting example be referred to as the first healthcare professional, operates an electronic user device $120_A$ on which a first client application $110_A$ is implemented. In this example, there is further a client user $121_B$, who may in this example be referred to as the second healthcare professional, who operates an electronic user device $120_B$ on which a second client application 1108 is implemented. Each of the first and second client applications $110_A$, $110_B$ has been paired with the host application 130 implemented on the host server 140 and communication of anonymous patient data in manners described herein is thereby enabled between the client and host applications. There is shown a healthcare monitoring system 100 for anonymous communication of patient data associated with a patient from a first electronic user device $120_A$ associated with a first client user $121_A$ to a second electronic user device $120_B$ associated with a second client user $121_B$, via a wireless network. The first electronic user device $120_A$ comprises a first client application $110_A$ and the second electronic user device $120_B$ comprises a second client application $110_B$. The system 100 further comprises a host server 140 having a host application 130. Each of the first and second client applications $110_A$, $110_B$ is configured to communicate with the host application 130 via the wireless network. The system 100 further comprises a respective memory, e.g., memories $150_A$, $150_B$, accessible by each of the first and second client applications, and a memory 160 accessible by the host application.

The system 100 is configured to pair each of the first and second client applications $110_A$, $110_B$ with the host application 130. Therefore, the host application 130 is configured to, for each of the first and second client user $121_A$, $121_B$ and respective first and second client application $110_A$, $110_B$:

generate a unique access key for the client user, wherein the unique access key comprises a first part K_1 and a second part K_2, wherein the first part of the unique access key is the original key and the second part of the unique access key is a hash or thumbprint of the original key, and wherein the unique access key, or any of its parts, cannot by themselves be linked to the client user;

store the second part of the unique access key in the memory accessible by the host application, wherein the second part is stored in association with information identifying the client user; and send the first part of the unique access key to the respective client application.

Each of the first and second client application are in turn configured to store the received first part of the unique access key in the memory accessible by the respective client application.

The first client application $110_A$ is further configured to send to the host application 130 the first part of the access key associated with the first client user $K\_1_A$, information $ID_B$ identifying the second client user, medical data MD concerning the patient and information $ID_{PAT}$ identifying the patient.

The host application 130 is configured to identify the first client user based on the received first part of the access key associated with the first client user and to identify the patient P by mapping the received information $ID_{PAT}$ identifying the patient to a list of patient identities stored in the memory of the host application. The information $ID_{PAT}$ identifying the patient may for example be name, social security number, a first part of an access key of a client application on an electronic user device of the patient that has been paired with the host application 130, or any other suitable information corresponding to the format of information in the list of patient identities stored in the memory of the host application. In one or more embodiments, the host application may be configured to identify the client user associated with the unique access key by generating a second part of the access key, based on the received first part of the access key associated with the client user; comparing the generated second part of the access key to one or more second parts of access keys stored in the memory accessible to the host application to find a matching second part, wherein the stored one or more second parts of access keys have been generated during pairing of the host application with one or more client applications; and if a matching second part of an access key is found, identifying the client user as the client user associated with the matching second part stored in the memory.

After identification of the patient P, the host application is configured to store the information identifying the second client in association with the medical data, to indicate that the second client is the person authorized to retrieve of receive the medical data. Thereby, the host application is enabled to send the medical data to the second client application upon a request therefrom.

The host application 130 is further configured to send patient data D' to the first client application $110_A$, wherein the patient data D' comprises the medical data MD concerning the patient P and an anonymous personal ID associated with the patient P, wherein neither the medical data MD nor the anonymous personal ID comprises any information identifying the patient. Thereby, the patient data D' cannot be linked to the patient P. Before sending the patient data D', the host application may be configured to generate an unreadable version of one or more part of the patient data D', e.g., by encryption. Thereby, the medical data, and optionally also the anonymous personal ID, are sent in a form that cannot be read without e.g., decryption using the proper key.

The first client application and the host application may be configured to obtain the anonymous personal ID associated with the identified patient by performing the steps 710 to 740 in connection with FIG. 7. Thereby, an anonymous personal ID associated with the identified patient is obtained that is later used for anonymous communication of medical data between the first and second client device.

Thereafter, the first client application $110_A$ is configured to send to a message comprising the patient data D' to the second client application $110_B$. As an alternative to sending patient data D' directly in the message, the message may contain a link to the patient data D' or it may be in a file attached to the message. Suitably, the anonymization and later de-anonymization of the medical data and the identity of the patient performed by the host application enables the communication between the first client application and the second client application to be performed over an open network as well, using any type of communication means, since the information transferred between the first and second client device cannot is not linked to any identity of the patient, or patients, to which the medical data relates.

The second client application $110_B$ is configured to receive the message and, in response to an input signal received in the second client application $110_B$ triggering opening of the received message, send the patient data D' to the host application 130 together with the first part of the access key $K\_1_B$ associated with the second client user. The host application 130 is in turn configured to identify the second client user based on the received first part of the access key associated with the second client user. If the identified second client user corresponds to the information identifying the second client stored in association with the medical data in the memory accessible to the host application, the host application is configured to send the stored medical data concerning the patient and information identifying the patient to the second client application. In this respect, the host application may be configured to decrypt or in other ways render the medical data and/or patient identity information readable before sending them to the second client application, if any or both of them have previously been made unreadable. Thereby, the receiving party can review the content of the patient data D' using the unique access key K only if the both the sending party, herein the first client application, and the receiver application, herein the second client application, have each been paired with the host application according to embodiments presented herein.

In another embodiments, at least one electronic user device and corresponding client application may function as either or both a sender and receiver of patient data, and the host server and host application may similarly function as either or both a sender and receiver of patient data. The purpose may for example be that a client user wants to use the client application on her/his respective electronic user device for sending patient data (relating to herself/himself, a patient in the care of the client user, or any other patient whose patient data the client user has legitimate access to) to the host server at one time. At another time, the same client user may want to access stored patient data associated with one or more patients, and therefore requests the host server to transfer this data to his/her electronic user device using the paired host application and client application. This manner of two-way patient data communication, relating to both sending and retrieval of patient data, is schematically illustrated in FIG. 6, as well as indicated by the arrows leading in both directions between client applications and the host application in FIG. 1 and FIG. 5.

In FIG. 6, a client user $121_C$ has an electronic user device 120c on which a client application $110_C$ is implemented. In this example, there is further a client user $121_D$ who has an electronic user device $120_D$ on which a client application $110_D$ is implemented. Each of the client applications $110_C$, $110_D$ has been paired with the host application 130 implemented on the host server 140 and communication of anonymous patient data in manners described herein is thereby enabled between the client and host applications.

In a third embodiment wherein a client user is interested in retrieving patient data relating to one or more patients from the host server, there is provided a healthcare monitoring system 100 for anonymous communication of patient data associated with at least one patient P from a host server 140, using a host application 130 implemented in the host server, to an electronic user device 120, using a client application 110 implemented in the electronic user device, via a wireless network 180. The electronic user device comprises a client application, the host server comprises a host application, and the client application is configured to communicate with the host application via the wireless network. The system further comprises a memory 150 accessible by the client application, and a memory 160 accessible by the host application. Similarly to the previous embodiments, the system is configured to pair the client application and the host application, by the host application being configured to:
    generate a unique access key for the client user, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client user;
    store the second part of the unique access key in the memory accessible by the host application, wherein the second part is stored in association with information identifying the client user; and
    send the first part of the unique access key to the client application;
The client application is in turn configured to receive the first part of the unique access key from the host application and store the received first part of the unique access key in the memory accessible by the client application.

In this embodiment, the client application is further configured to send to the host application a request to retrieve patient data from the host server, the request comprising a specification of the patient data to be retrieved and the first part of the access key associated with the client user. The specification indicates which data is to be retrieved and for which patient(s). No information identifying the patient(s) is sent, only ID:s, e.g., in the form of the respective first part of an access key associated with the patient that was previously generated through pairing of the host application and a client application implemented on an electronic user device of the patient. Of course, the respective unique ID may be other anonymous patient ID information associated with the respective patient that in itself cannot be linked to the patient, as described herein. In any of these cases, the host server comprises information for converting the ID, i.e., the anonymous information associated with the respective patient, to an identification of the patient.

In response to receiving the request, the host application is configured to identify the client user associated with the unique access key, by generating a second part of the access key, based on the received first part of the access key and comparing the generated second part of the access key to one or more second parts of access keys stored in the memory accessible to the host application to find a matching second part, wherein the stored one or more second parts of access keys have been generated during pairing of the host application with one or more client applications. If a matching second part of an access key is found, the host application is configured to identify the client user as the client user associated with the matching second part stored in the memory.

After identification of the client user, the host application is configured to check if the identified client user is authorized to retrieve the requested patient data. If the identified client user is authorized to retrieve the requested patient data, the host application is further configured to send the requested patient data from the host application to the client application, wherein the patient data does not comprise any information identifying the at least one patient.

Thereby, a client user is enabled to retrieve patient data only if she/he is authorized to do so, according to access rules stored in the memory accessible to the host application. Furthermore, when the requested patient data is sent to an authorized client user's client application, no information identifying the patient or patient associated with the patent data is included. Thereby, secure anonymous communication of the sensitive data is enabled.

Also in this third embodiment, the client application may be configured to authenticate the client as an authorized user of the client application, using strong authentication, prior to the pairing of the client application and the host application.

In order to generate a unique access key for the client user the host application may also in this embodiment be configured to generate a randomized numeric code that is unrelated to any information identifying the client user; wherein the client application is configured to receive the randomized numeric code from the host application and send a message in the form of a control signal to the host application in response to receiving the unique access key; and the host application is configured to receive the control signal from the client application and generate the unique access key in response to receiving the control signal.

In any embodiment, the patient data D, D' may further be encrypted before sending.

Instead of a first and second healthcare professional, many other sending and receiving parties are of course feasible for communication of patient data D, depending on the circumstances. Any, or both, of the sending and receiving party may e.g., be a patient, a healthcare professional, a social care professional, a representative of the pharmaceutical industry, a representative of the academy such as a researcher, or any other party having a legitimate interest in sending or receiving patient data D. The secure communication of the present invention is enabled, in one or both directions, by embodiments described herein including pairing of the sender application and the receiver application.

Any advantages described herein in connection with embodiments of one aspect of the invention, such as a system or method, are equally applicable to the corresponding described embodiments of any other aspects of the invention, including systems, methods, computer programs, and non-volatile data carriers.

Method Embodiments

Method embodiments corresponding to the system embodiments will now be described in connection with FIGS. 2, 3, 4, 7, 8 and 9.

Figure 2:
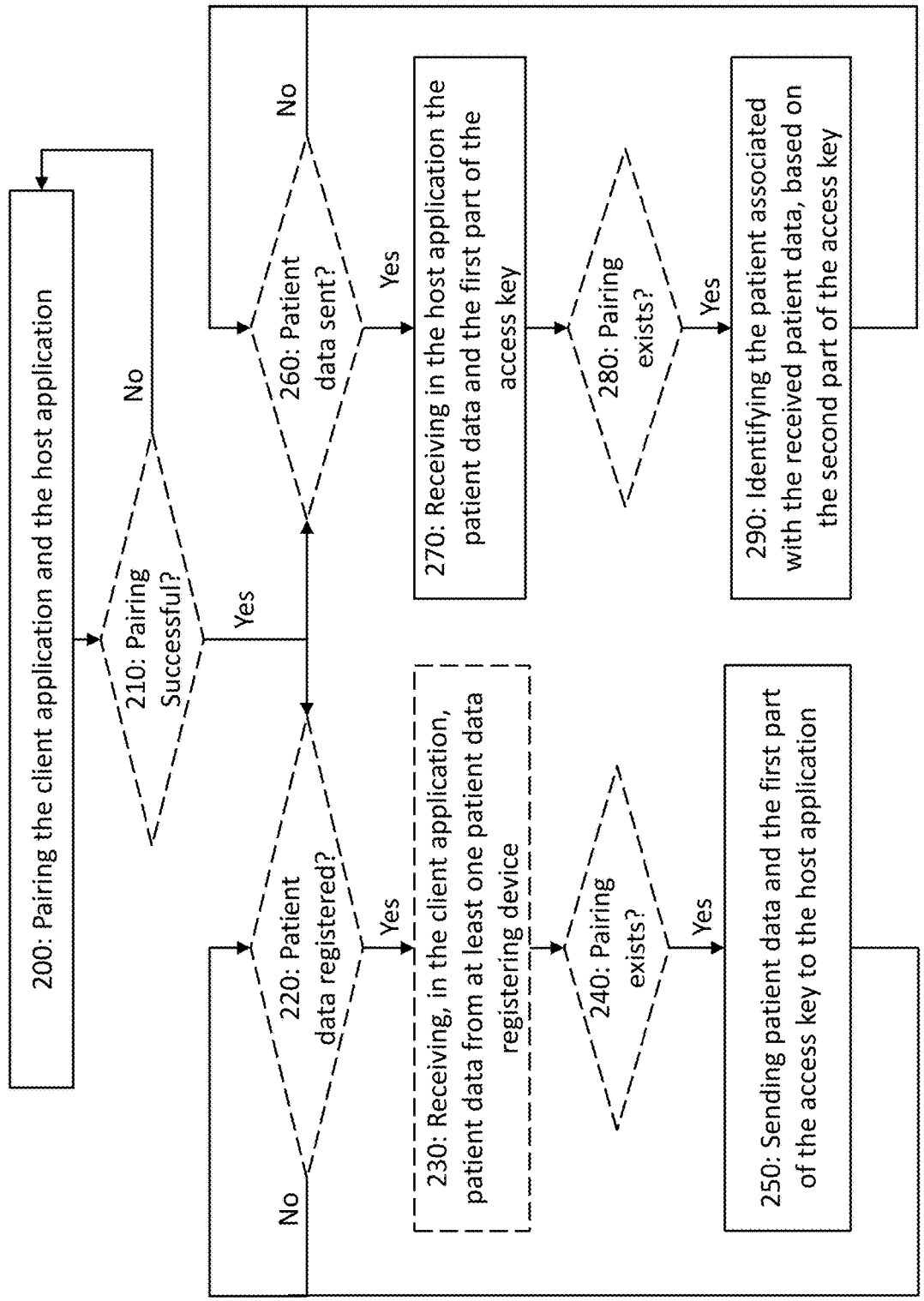
FIG. 2 shows a flow diagram illustrating a process for secure communication of digital information, comprising steps according to one or more method embodiments of the invention.

FIG. 2 shows a flow diagram illustrating one or more embodiments of a method/process in a healthcare monitoring system 100 for anonymous communication of patient data D, associated with a patient P, from an electronic user device 120, using a client application 110 implemented in the electronic user device 120, to a host server 140, using a host application 130 implemented in the host server 140, via a wireless network 180, and further for identification of the patient P, associated with the patient data D, after the patient data D is received in the host server 140. This method corresponds to the first embodiment of the system described in connection with FIG. 1, wherein the client user is the patient P.

According to one or more embodiments illustrated by FIG. 2, the method comprises:

In step 200: Pairing the client application 110 and the host application 130.

Of course, a host application 130 can be paired with one or more client applications 110, for receiving patient data from corresponding one or more client users, in this embodiment being the patients.

In an optional step 210: Checking if the pairing in step 200 was successful.

According to embodiments wherein the method step 210 of checking whether the pairing in step 200 was successful is performed:
 if the pairing was not successful, the method returns to step 200 to allow for another, optional, paring attempt; or
 if the pairing was successful, the method continues according to step 220 and step 260, respectively.

Steps 220-250 below describe the method steps performed by the client application 110, and steps 260-290 describe the method steps performed by the host application 130.

In one or more embodiments, the client application 110 is configured to perform any or all of the method steps 220-250.

In one or more embodiments, the host application 130 is configured to perform any or all of the method steps 220-250.

In an optional step 220: Checking whether patient data D has been registered.

The patient data D may have been registered by at least one patient data registering device 170, wherein the at least one patient data registering device 170 may comprise a selection of the following: one or more sensors for blood pressure rate, heart rate, breath rate, ECG/EKG (electrocardiogram), respirations, blood oxygen levels, blood temperature, spirometer, or medtech equipment (ultra sound, patient monitor anesthesia, X-Ray mobile, oxygen concentrator, coagulometer, scale for adults, CT-scanner, one or more digital forms, or applications such as e.g. Health Kit or Google Fit.

According to embodiments wherein the method step 220 of checking whether patient data D has been registered is performed:
 if no patient data D has been registered, the method returns to step 220; or
 if patient data D has been registered, the method continues according to step 230.

In an optional step 230: Receiving, in the client application 110, patient data D from at least one patient data registering device 170.

Receiving patient data D may also be referred to as new relevant data being generated in the client application 110.

In an optional step 240: Checking whether a pairing exists between the client application 110 and the host application 130.

Reasons that a pairing may no longer exist are e.g. that: pairing between the host application 130 and client application 110 has been terminated either by the client user deleting the client application 110 from her smartphone or other electronic user device 120 where the client application 110 has been installed; the healthcare provider deleting the client user in the host application 130 by deleting the second part K_2 (e.g. the hash) of the unique access key K that is related to/associated with the client user identifying information; or due to an error.

According to embodiments wherein the method step 210 of checking whether a pairing exists between the client application 110 and the host application 130 is performed the method comprises:
- if no pairing exists, the method ends and no further patient data D is communicated from the client application 110 to the host application 130; or
- if a pairing exists, the method continues according to step 250.

In step 250: Sending patient data D and the first part K_1 of the access key K to the host application 130, wherein the patient data does not comprise any information identifying the patient.

The patient data D may be the received patient data if optional step 230 has been performed. In this case, sending the patient data D and the first part K_1 of the access key K to the host application 130 is done in response to receiving patient data D in the client application 110.

As mentioned in connection with FIG. 4, information is hereafter securely and automatically transferred, according to the client application 110 configuration, between the client application 110 and the host application 130.

According to different settings or configurations of the client application 110, patient data D may be sent/transferred to the host application 130 continuously, at certain time intervals, only at certain times, e.g., only at night, or according to any other suitable rules/configuration depending on the circumstances.

In an optional step 260: Checking whether patient data D has been sent from the client application 110 to the host application 130.

Worded differently, optional step 260 comprises checking whether patient data D has been received in the host application 130, from the client application 110.

According to embodiments wherein the method step 260 of checking whether patient data D has been sent is performed the method comprises:
- if patient data D has not been sent, the method repeats step 260; or
- if patient data D has been sent, the method continues according to step 270.

In step 270: Receiving in the host application 130 the patient data D and the first part K_1 of the access key K.

In step an optional step 280: Checking whether a pairing exists between the patient application 110 and the host application 130.

According to embodiments wherein the method step 280 of checking whether a pairing exists between the client application 110 and the host application 130 has been performed the method comprises:
- if no pairing exists, the method ends; or
- if a pairing exists, the method continues according to step 290.

In step 290: Identifying the patient P associated with the received patient data D, based on the second part of the access key K.

Since the client user is in this embodiment the patient P associated with the received patient data D, step 290 may comprise:
- identifying, using the host application, the patient associated with the received patient data as the client user associated with the unique access key, by: generating a second part of the access key, based on the received first part of the access key;
- comparing the generated second part of the access key to one or more second parts of access keys stored in the memory accessible to the host application to find a matching second part, wherein the stored one or more second parts of access keys have been generated during pairing of the host application with one or more client applications; and
- if a matching second part of an access key is found, identifying the patient as the client user associated with the matching second part stored in the memory.

Turning now to FIG. 7, there is shown a flow diagram of a method in a healthcare monitoring system 100 for anonymous communication of patient data associated with a patient, from the electronic user device, using the client application 110 implemented in the electronic user device, to the host server, using the host application 130 implemented in the host server, via a wireless network, and identification of the patient associated with the patient data after the patient data is received in the host server.

Step 200 of pairing the client application and the host application as well as the optional steps 210, 240 and 280 are identical to the corresponding steps described in connection with FIG. 2. The method may also, even if not shown in the figure, comprise the steps 220, 230 and 260, in embodiments wherein the electronic user device 110 is configured to register patient data in any manner described herein.

The method is in other parts similar to the method described in connection with the FIG. 2. Like the method of FIG. 2, in order to be able to send information of who the patient is in an anonymous and thereby secure manner, the patient identity further needs to be anonymized before the patient data is transferred, and then deanonymized by the host application 130 after it receives patient data from the client application 110. However, in the method shown in FIG. 7, the client user, using the client application in her/hos electronic user device, is not the patient and it is therefore not enough to identify the client user associated with the unique access key to find the identity of the patient associated with the transferred patient data. Therefore, the method of FIG. 7 comprises a first step of providing an anonymous patient ID, e.g., a random number, a code or any other suitable information that is not linked to the patient identity and from which the patient identity cannot be derived. The anonymous patient ID may already be stored in the memory of the host application 130 in association with the patient identity and be retrieved therefrom. Alternatively, the anonymous patient ID may be generated and stored in the memory of the host application 130 in association with the patient identity. The method then comprises sending the patient data together with the anonymous patient ID from the client application 110 to the host application 130, and finally identifying, in the host application 130, the patient associated with the patient data by mapping the anonymous patient ID to the patient identity associated therewith.

In more detail, the method comprises:

In step 710: Sending information identifying the patient and the first part of the access key associated with the client user from the client application 110 to the host application 130.

In step 715: Checking if information identifying a patient and the first part of an access key has been received in the host application 130.

In response to receiving the information identifying a patient and the first part of an access key in the host application 130, the method continues in step 720.

In step 720: Identifying, using the host application 130, the client user associated with the unique access key.

Identifying the client user associated with the unique access key in step 720, using the host application, may comprise:

generating a second part of the access key, based on the received first part of the access key associated with the client user, if this has been sent, or otherwise using the first part of the access key generated through pairing of the client application of the client user and the host application;

comparing the generated second part of the access key to one or more second parts of access keys stored in the memory accessible to the host application to find a matching second part, wherein the stored one or more second parts of access keys have been generated during pairing of the host application with one or more client applications; and if a matching second part of an access key is found, identifying the client user as the client user associated with the matching second part stored in the memory.

In response to identifying the client user, the method continues in step 730.

In step 730: Identifying, by the host application 130, the patient by mapping the received information identifying the patient to a list of patient identities stored in the memory of the host application 130.

The patient data to be sent may relate to more than one patient, i.e., it may relate to at least one patient, wherein step 730 is performed for each of the at least one patient until all patients have been identified.

In step 740: Sending an anonymous personal ID associated with the identified patient from the host application 130 to the client application 110.

The anonymous personal ID associated with the identified patient may already be stored in association with the patient identity in the memory accessible to the host application 130, or a new anonymous personal ID may be generated in response to identifying the patient and stored in association with the patient identity in the memory accessible to the host application 130.

Thereby, the anonymous information can be used in further anonymous and hence secure sending of data or requesting of data related to at least one patient, even if the client user is not the patient.

If the patient data to be sent relate to more than one patient step 740 is performed for each of the patients by sending an anonymous personal ID associated with each of the identified patient from the host application 130 to the client application 110.

Optionally, the method may further comprise a step of checking if at least one anonymous personal ID has been received in the client application before step 750 is performed.

In an optional step 240: Checking whether a pairing exists between the patient application 110 and the host application 130.

According to embodiments wherein the method step 240 of checking whether a pairing exists between the client application 110 and the host application 130 has been performed the method comprises:

if no pairing exists, the method ends; or
if a pairing exists, the method continues according to step 750.

In step 750: sending patient data D from the client application 110 to the host application 130, wherein the patient data D comprises medical data concerning the patient and the anonymous personal ID for the patient, wherein neither the patient data nor the personal ID for the patient comprise any information identifying the patient.

Since the patient data to be sent may relate to one or more patients, i.e., at least one patient, the patient data D may comprise medical data concerning each of the at least one patient and the corresponding at least one anonymous personal ID associated with the medical data of each of the at least one patient.

Since no information identifying the patient, or patients, is transferred as part of the patient data D, the transfer is anonymous and secure.

In an optional step 280: Checking whether a pairing exists between the patient application 110 and the host application 130.

According to embodiments wherein the method step 280 of checking whether a pairing exists between the client application 110 and the host application 130 has been performed the method comprises:

if no pairing exists, the method ends; or
if a pairing exists, the method continues according to step 760.

In step 760: checking if patient data D has been received in the host application 130.

In step 770: identifying, using the host application 130, the patient associated with the received patient data based on the received anonymous personal ID for the patient.

If the received patient data relates to more than one patient step 770 is performed for each of the patients by identifying, using the host application 130, each patient associated with parts of the medical data in the received patient data, based on each received anonymous personal ID, and the indications of which medical data is associated with each received anonymous personal ID.

Thereby, the system 100 is enabled to deanonymize the patient data D after it has been received in the host application 130 from the client application 110.

Figure 8:
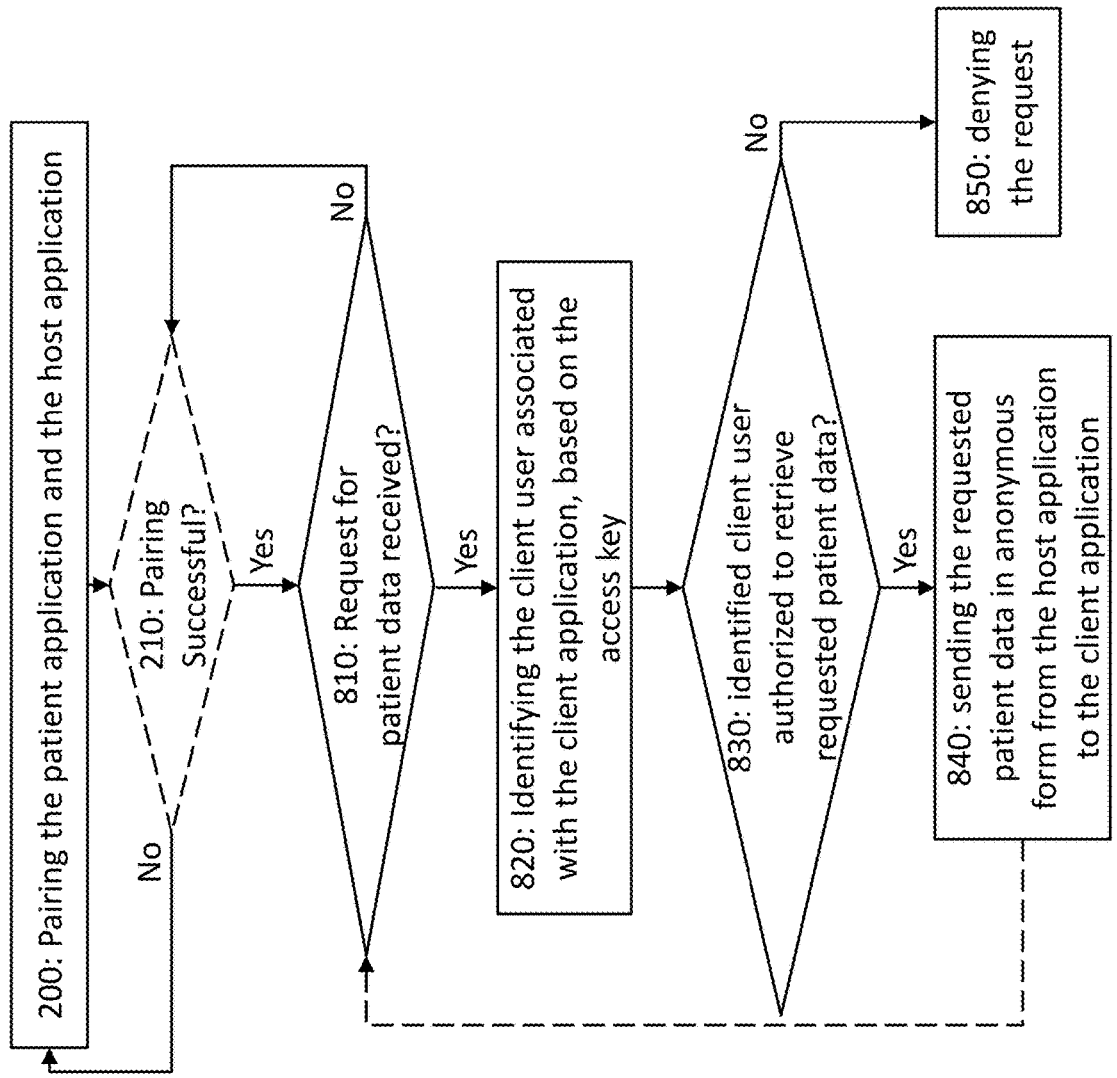
FIG. 8 shows a flow diagram illustrating a process for secure communication of digital information, comprising steps according to one or more method embodiments of the invention.

As indicated in FIG. 8 by the dashed arrows, the method may be performed iteratively. For example, if not all patient data has been received in the host application 130 from the client application 110, the method may return from step 760 to step 770.

Alternatively, or additionally, if another access key and information identifying a patient is received in the host application 130, the method may return to from step 770 to step 715. Alternatively, or additionally, the method may return from step 770 to step 710, thereby starting over the method of FIG. 7.

Figure 3:
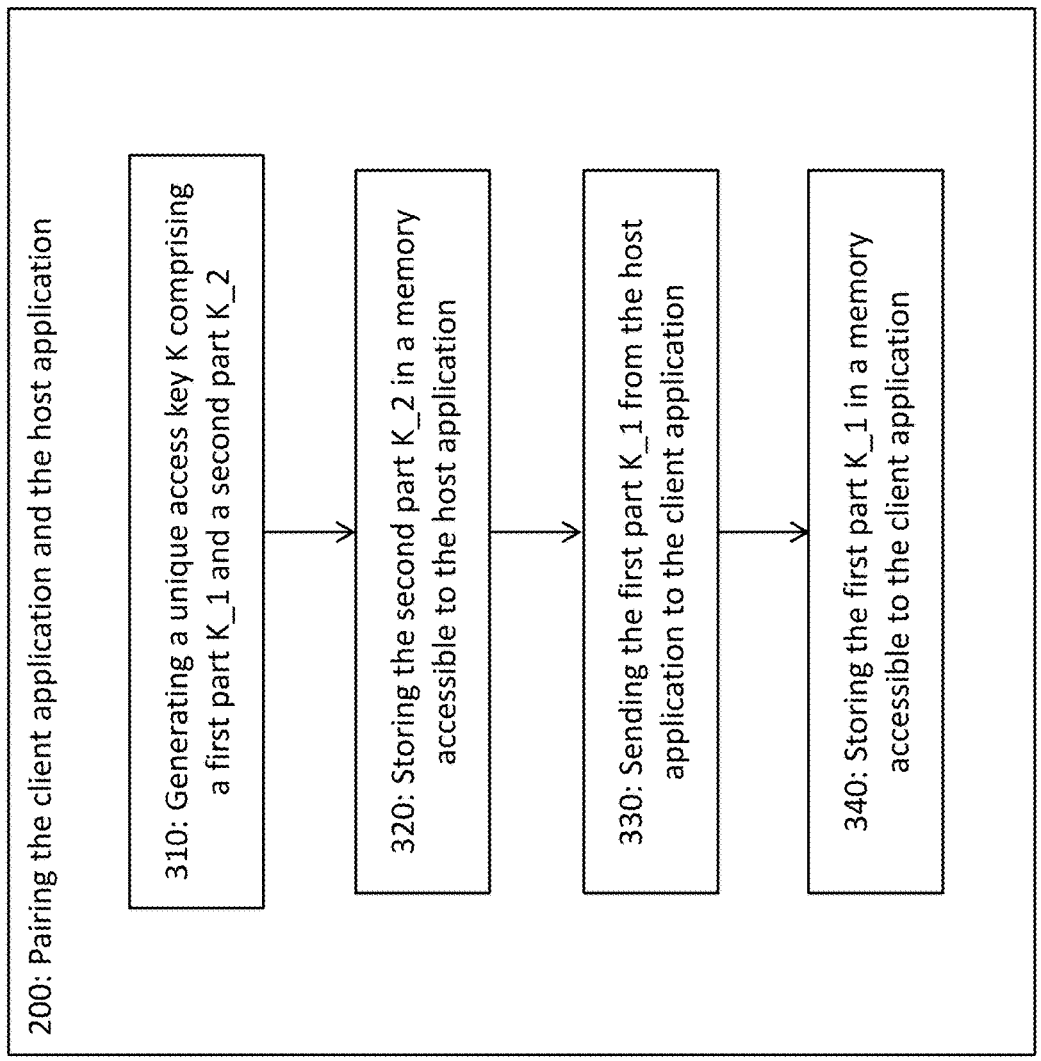
FIG. 3 shows a flow diagram illustrating one or more embodiments of the proposed method.

In one or more embodiments, of either of the method embodiments described in connection with FIGS. 2 and 7, the pairing of step 200 comprises sub-steps 310-340 shown in FIG. 3, wherein the method comprises:

In sub-step 310: Generating a unique access key K for the client user, using the host application 130, wherein the unique access key K is in itself unrelated to any information identifying the client user, in this embodiment the patient P, wherein the unique access key K comprises a first part K_1 and a second part K_2.

Sub-step 310 of generating a unique access key K for the client user may in turn comprise:

generating, using the host application 130, a randomized numeric code C that is unrelated to any information identifying the client user;
receiving, in the client application 110, the randomized numeric code C;
sending a message in the form of a control signal S1 from the client application 110 to the host application 130 in response to receiving the unique access key K;
receiving, in the host application 130, the control signal S1; and
generating, in the host application 130, the unique access key K in response to receiving the control signal S1.

In any embodiment described herein comprising generation of a randomized code C, the randomized numeric code C may be received in the client application 110 in response to a user, i.e., the client user, registering/inputting the code using one or more input devices (not shown in the figure) that is/are integrated in, connected to or communicatively coupled to the electronic user device 120. The one or more input devices may e.g., be in the form of a keyboard, touch functionality, speech to text functionality, or any other suitable input device known in the art. According to different embodiments, the randomized numeric code C may, before it is input into the client application 110, be communicated to the client user orally by the medical staff/caregiver/host, or sent as a digital signal from the host application 130 to the client application 110, using any suitable communication protocol and communication method known in the art. As non-limiting examples, the randomized numeric code C could be sent in the form of a short message service (SMS), e-mail, or a message in the client application interface.

Method step 310 may further comprise, and the host application 130 may further be configured to, setting/configuring the numbers of digits in the randomized numeric code C and/or the length of time of validation of the randomized numeric code C.

In sub-step 320: Storing the second part K_2 of the unique access key K in a memory 160 accessible to the host application 130, wherein the second part K_2 is stored in association with information identifying the client user.

In sub-step 330: Sending the first part K_1 of the unique access key K from the host application 130 to the client application 110.

In sub-step 340: Storing the first part K_1 of the unique access key K in a memory 150 accessible to the client application 110.

In some embodiments, wherein the client user is the patient P, identifying the patient P associated with the received patient data D, based on the second part K_2 of the access key K comprises:
  generating a second part K_2 of the access key K, based on the received first part K_1 of the access key K;
  comparing the generated second part K_2 of the access key K to one or more second parts of access keys stored in the memory 160 accessible to the host application 130 to find a matching second part, wherein the stored one or more second parts of access keys have been generated during pairing of the host application 130 with one or more client applications 110; and
  if a matching second part of an access key is found, identifying the patient P as the client user associated with the matching second part stored in the memory (160).

A substantial advantage of using a unique access key K that is unrelated to any information identifying the client user, when the client user is the patient P, is that the access key K, or any of its parts K_1 and K_2, cannot by themselves be linked to the patient P. Should the patient data D fall into the hands of someone other than the intended user of the host application or host server, the patient's identity is thereby protected.

In one or more embodiments, the first part K_1 of the unique access key K is the original key and the second part K_2 of the unique access key K is a hash or thumbprint of the original key.

The method may comprise, to generate the second part K_2 of the access key K based on the received first part K_1 of the access key K, running a mathematical function on the first part K_1.

The host application 130 may correspondingly be configured to run a mathematical function on a first part K_1 of a unique access key K to generate a second part K_2 of the unique access key K.

The method according to any of the embodiments presented herein may further comprise, prior to pairing the patient application 110 and the host application 130:
  authenticating a host user as an authorized user of the host application 130, using strong authentication; and
  authenticating a client user as an authorized user of the client application 130, using strong authentication.

Authenticating the host user may be performed using the host application 130, e.g., during login.

Authenticating the client user may be performed using a client application 110, e.g., during login. Alternatively, authenticating the client user may be performed by identifying the client user at the check-in desk in a hospital or the like, by using a driver's license, passport or similar.

The method according to any of the embodiments presented herein may further comprise storing the received patient data D in the memory 150 accessible to the client application 110.

FIG. 4 shows a flow diagram illustrating a process for secure communication of digital information, comprising steps according to one or more embodiments of the proposed method described in connection with FIGS. 2, 3 and 7. The patient in the description of FIG. 4 below corresponds to the patient P.

The process of applying secure communication by transferring information that does not include personal or individual identity information consist of a number of steps.

Below, the process of secure communication illustrated in FIG. 4 is described in more detail:

1. The patient connector (PC) is imported both into the host application and into the client application. Referring to the reference numbers in FIG. 4, this is step 1.
2. The PC is customized in the host application
   a. Configuring the numbers of digits in the randomized code
   b. Length of time of validation of the randomized code
   Referring to the reference numbers in FIG. 4, this is step 2.
3. In the client application it is configured when information should be transferred between the client application and host application. Referring to the reference numbers in FIG. 4, this is step 3.
4. Identification
   a. The at least one client user, e.g., patient, is securely identified at the check-in desk in a hospital by using a driver's license or similar identification. Alternatively, the client user is identified via login using strong authentication in the client application.
   b. The host user, e.g., medical staff, is securely identified via login using strong authentication in the host application.
   Referring to the reference numbers in FIG. 4, this is step 4. As can be seen from step 4 in FIG. 4, the identification of the patient can be performed e.g., in the hospital reception or via the client application. Further applicable options are presented in connection with FIG. 2.
5. The host user may ask the client user to download the patient app in her smartphone during the physical meeting, or via electronic communication.
6. The host user may ask the client user to open the client application in her smartphone during the physical meeting. The at least one client user installs and opens their client application on their respective electronic user device. Referring to the reference numbers in FIG. 4, this is part of step 5.

7. The host user generates a randomized set of numbers (i.e., a random code) for the specific client user, using the host application. The host application generates the randomized set of numbers through the imported PC. Referring to the reference numbers in FIG. 4, this is part of step 6. This corresponds to generating the randomized numeric code C according to embodiments presented herein.

8. The host user forwards the given randomized set of numbers to the client user either orally during the meeting in person, or the host application sends it digitally to the electronic user device (to client application, via sms, via email, or via other communications channel). Referring to the reference numbers in FIG. 4, this is part of step 6.

9. The at least one client user records the respective randomized set of numbers in their client application, or the respective client application stores the respective random code directly if received in the client application from the host application. Referring to the reference numbers in FIG. 4, this is step 7.

In other words, the randomized numeric code C may be communicated directly from the host application 130 and received in the patient application, according to embodiments presented herein.

10. A technical pairing is made between the host application and the client application. Referring to the reference numbers in FIG. 4, this is part of step 8. This corresponds to the pairing described in connection with FIG. 2 and other embodiments herein.

11. Information is hereafter securely and automatically transferred according to the PC configuration between the client application and the host application. In other words, anonymized data is sent continuously and interactively hereafter between the client application and the host application (sent from client application to host application, or requested and retrieved from host application to client application) or sent between client applications that have both been paired with the host application, using the same access key(s) and turned towards the same hash(es) on each occasion. The sensitive data sent in any of these communication manners does not include any personal or individual identity information during the transfer of information over the Internet or any other network and therefore provides secure, anonymized, communication. Referring to the reference numbers in FIG. 4, this is part of step 8 and step 9.

12. The pairing between the host application and client application is terminated when either:
    a. The client user deletes the client application from her electronic user device, or
    b. The host user deletes the client user in the host application by deleting the hash that is related to the client user. Referring to the reference numbers in FIG. 4, this is step 10.

Login into the client application, by the client user, may include entering/inputting a password or other data that is unrelated to the client user's identity. This is preferable compared to using e.g., Bank ID or other methods that are linked to the user's identity, and therefore potentially could be used to identify the client user who is using the client application and sending her confidential data.

How the technical pairing between the host application and the client application may be conducted is described in more detail below:

i. The host user, e.g., a medical staff, requests a randomized set of numbers for the identified client user, e.g., a patient, in front of her, in the host application.

ii. An ID is created in the host application for this specific client user. This ID is not based on a personal ID and cannot be linked to a client user's identity.

iii. When the randomized set of numbers, that has been given orally or via the electronic user device to the patient, is registered in the client application, the PC in the client application sends a message to the PC in the host application.

iv. When the host application receives the message the PC in the host application generates an access key that is sent to the client application;
    a. The access key is made up of two parts: a) an original key that the client application holds and b) a hash of the original key that the host application holds.
    b. The PC in the host application runs a mathematical function on the access key when received from the client application. The mathematical function generates the hash of the original key.

This access key corresponds to the unique access key K, having the two parts K_1 and K_2, according to embodiments presented herein.

v. A hash/thumbprint of the access key that has been is stored in the host application; (it is a hash/thumbprint of the access key sent to the client application)

vi. Every time the client application transfers data to the host application the access key is accompanied/sent together with this transfer vii. When the host application receives the message from the client application the received accompanied access key is run through a mathematical function. The outcome from running the access key through the mathematical function is this client user's hash.

viii. This hash/thumbnails is compared with the hashes stored in the host application to look up a match and the identification of the client user that has sent the data. This is an embodiment of how to identify the patient P associated with the received patient data D, if the client user is the patient P, based on the second part K_2 of the access key K, as described herein.

The patient connector is configured with anything from 1 to an infinite number of digits. Recommended is to provide with a random code consisting of at least 8 digits. To perform the pairing, the code is given by word of mouth from for instance a medical professional working in the host application to a patient or other client user.

The client user to pair must enter the numeric code into her client application in her smartphone or other electronic user device. Alternatively, the numeric code is communicated directly from the host application 130 to the client application according to any of the embodiments presented herein. According to some embodiments, the client application must call the host server code within a certain time, otherwise the code is invalid. The duration may be set to 30 minutes, or any other suitable duration depending on circumstances.

The code is checked and if it is valid it is paired to the identity of a client user on the application and an access key is generated. This access key is returned to the client application. A hash of the access key is stored on the host application; it is used to derive which patient it is that has communicated data from a client application to the host application. The solution has thus achieved a connection between a client application and a caregiver's host application. The access key itself does not contain any information about to whom the information sent belongs. Future connections between the client application and the caregiver's host application will use the same access key every time a transfer is made, enabling the host application to always know from which client user, e.g., patient, the data is sent.

The secure communication will advantageously be exercised in a computerized system and/or through the internet or any other network.

The PC will advantageously be utilized within any work in society that can benefit from continuous access to secure and accurate individual registered data.

Turning now to FIG. 8, there is shown a flow diagram of a method in a healthcare monitoring system 100 for anonymous communication of patient data associated with at least one patient from a host server, using a host application implemented in the host server, to an electronic user device, using a client application implemented in the electronic user device, via a wireless network. In other words, FIG. 8 describes the transfer of patient data from the host application 130 to at least one client application 110. As described below, the transfer of patient data will not be initiated until a request has been received the (each of the at least one) client application 110 and it has been determined that the (each of the at least one) client user is authorized to receive the requested patient data. Furthermore, the patient data is in likeness with the other embodiments herein anonymized before sending and deanonymized after receival.

Step 200 of pairing the client application and the host application as well as the optional step 210 are identical to the corresponding steps described in connection with FIG. 2.

The method according to these embodiments further comprises:

In step 810: Sending, from the client application 110 to the host application 130, a request to retrieve patient data from the host server 130, the request comprising a specification of the patient data to be retrieved and the first part of the access key associated with the client user.

The specification indicates which data is to be retrieved and for which patient(s). In a non-limiting example, the client application may request to see certain specified medical data for all patient having surnames that start with the letter G, having one on a list of social security numbers, etc. However, no information identifying the patient(s) is sent as part of the request, only anonymous patient ID or ID:s.

The anonymous patient ID may already exist and be known to both the client application 110 and the host application 130. If the anonymous patient ID does not already exist that is known to both the client application 110 and the host application 130, an anonymous patient ID may be obtained as described in steps 710 to 740 in connection with FIG. 7.

The anonymous patient ID may e.g., be in the form of the respective first part of an access key associated with the patient, which was previously generated through pairing of the host application and a client application implemented on an electronic user device of the patient. Alternatively, the respective unique ID may be any other anonymous information associated with the respective patient that in itself cannot be linked to the patient, such as a random code, that is stored in the memory of the host application 130 in association with the patient identity. In any of these cases, the host server comprises information for converting the ID, i.e., the anonymous information associated with the respective patient, to an identification of the patient.

In step 820: Identifying, using the host application 130, the client user associated with the unique access key associated with the client user.

Step 820 is performed in response to receiving the request in the host application 130.

Identifying the client user in step 820 may comprise:
generating a second part of the access key, based on the received first part of the access key;
comparing the generated second part of the access key to one or more second parts of access keys stored in the memory accessible to the host application to find a matching second part, wherein the stored one or more second parts of access keys have been generated during pairing of the host application with one or more client applications; and
if a matching second part of an access key is found, identifying the client user as the client user associated with the matching second part stored in the memory.

In step 830: Checking, using the host application, if the identified client user is authorized to retrieve the requested patient data.

The check is performed by matching the client user identity and the requested patient data to preset access rules and conditions of the system 100.

If the client user is not authorized to retrieve the requested patient data, the method continues in step 850.

If the client user is authorized to retrieve the requested patient data, the method continues in step 840.

In step 840: Sending the requested patient data from the host application to the client application, wherein the patient data does not comprise any information identifying the at least one patient associated with the patient data.

In step 850: Denying the request to retrieve patient data.

By applying the method of FIG. 8, it is ensured that only a client user that is authorized to access certain patient data is able to retrieve it. It is further ensured that the patient data is transferred in an anonymous and secure manner in likeness with all the other embodiments herein.

Figure 9:
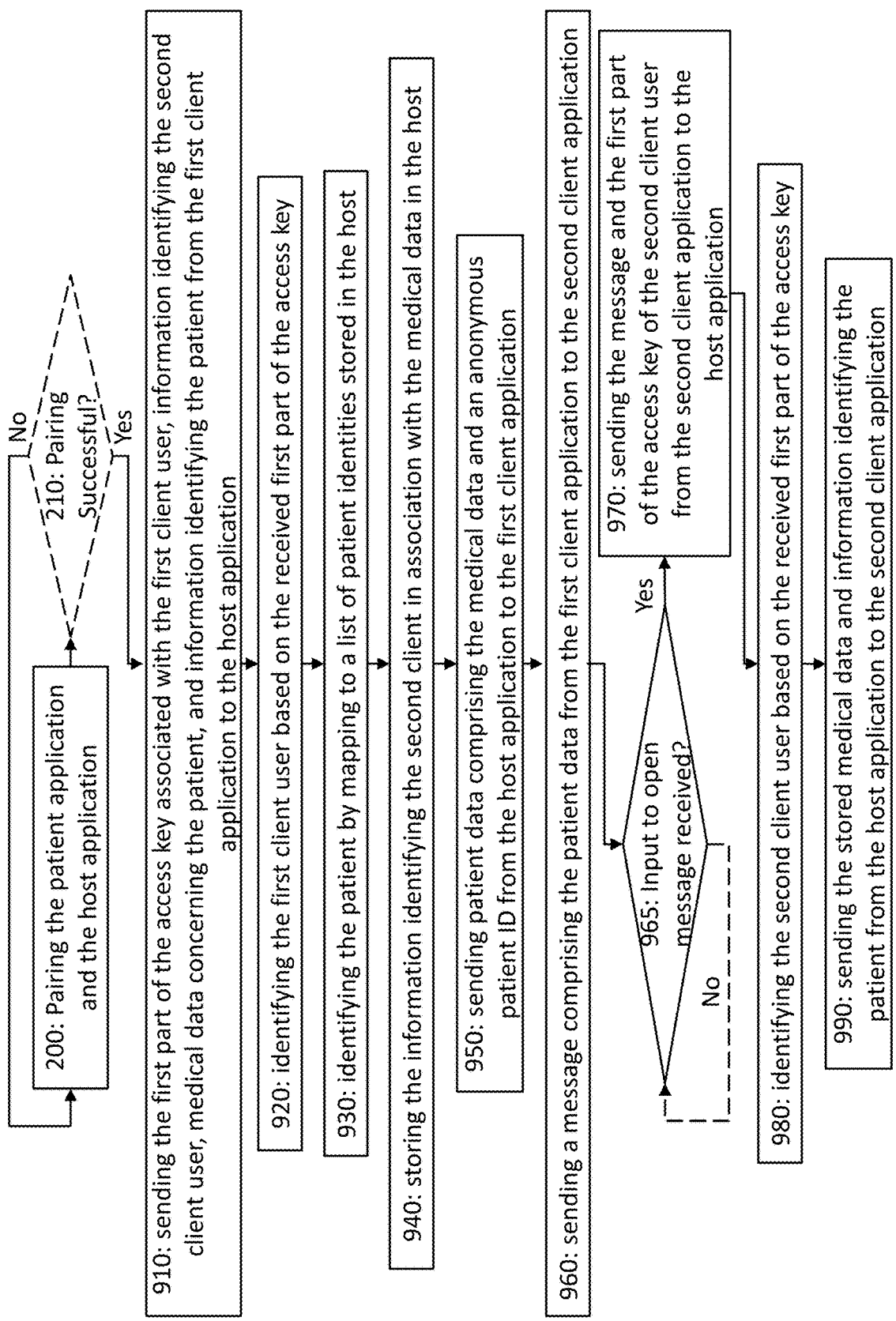
FIG. 9 shows a flow diagram illustrating a process for secure communication of digital information, comprising steps according to one or more method embodiments of the invention.

FIG. 9 shows a flow chart of a method in a healthcare monitoring system for anonymous communication of patient data associated with a patient from a first electronic user device, using a first client application implemented in the first electronic user device, to a second electronic user device, using a second client application implemented in the second electronic user device, via a wireless network. This method embodiment corresponds to the system embodiment described in connection with FIG. 5, wherein each of the first and second client applications $110_A$, $110_B$ has been paired with the host application 130 implemented on the host server 140 and communication of anonymous patient data in manners described herein is thereby enabled between each client application and the host applications. The method embodiments in connection to FIG. 9 relate to when the first client applications $110_A$ is used for sending patient data in an anonymous and secure manner to the second client application $110_B$, and enabling the second client application $110_B$ to deanonymize the received patient data, via interaction with the host application 130.

Step 200 of pairing the client application and the host application as well as the optional step 210 are identical to the corresponding steps described in connection with FIG. 2.

The method comprises:

In step 910: Sending from the first client application $110_A$ to the host application 130 the first part of the access key $K\_1_A$ associated with the first client user $121_A$, information $ID_B$ identifying the second client user $121_B$ as the intended recipient, medical data MD concerning at least one patient, and information $ID_{PAT}$ identifying the at least one patient associated with the medical data MD or respective parts of the medical data MD.

In step 920: Identifying, using the host application 130, the first client user 121$_A$ based on the received first part of the access key K_1$_A$ associated with the first client user.

Identifying, the client user in step 920 may comprise:
generating a second part of the access key, based on the received first part of the access key associated with the client user;
comparing the generated second part of the access key to one or more second parts of access keys stored in the memory accessible to the host application to find a matching second part, wherein the stored one or more second parts of access keys have been generated during pairing of the host application with one or more client applications; and
if a matching second part of an access key is found, identifying the client user as the client user associated with the matching second part stored in the memory.

In response to identifying the first client user 121$_A$, the method continues in step 930.

In step 930: Identifying, by the host application 130, each of the at least one patient by mapping the received information identifying each of the at least one patient to a list of patient identities stored in the memory of the host application 130.

In step 940: Storing the information identifying the second client user 121$_B$ in the memory of the host application 130, in association with medical data MD.

This indicates that the second client user 121$_B$ is the intended recipient of the medical data MD and the information of which patient(s) is/are associated with the medical data. In other words, it is comparable to an authorization to access this data.

In step 950: Sending patient data D' from the host application 130 to the first client application 110$_A$, wherein the patient data D' comprises the medical data MD concerning the at least one patient and the anonymous personal ID associated with each at least one patient, wherein neither the medical data MD nor the anonymous personal ID comprises any information identifying each of the at least one patient.

Thereby, the patient data D' cannot be linked to the patient P.

Before sending the patient data D', the method may comprise generating an unreadable version of one or more part of the patient data D', using the host application 130, e.g., by encryption. Thereby, the medical data MD, and optionally also the anonymous personal ID/IDs, are sent in a form that cannot be read without e.g., decryption using the proper key.

In step 960: Sending a message comprising the patient data from the first client application 110$_A$ to the second client application 110$_B$.

Suitably, the anonymization and later de-anonymization of the medical data and the identity of the patient performed by the host application enables the communication between the first client application and the second client application to be performed over an open network as well, using any type of communication means, since the information transferred between the first and second client device cannot is not linked to any identity of the patient, or patients, to which the medical data relates.

In step 965: Checking if input triggering opening of the message has been received in the second client application 110$_B$.

If input triggering opening of the message has been received in the second client application 110$_B$ the method continues with steps 970 and 980.

If no such input has been received, the method may comprise repeating step 965, as indicated by the dashed arrow in FIG. 9.

In step 970: Sending the message from the second client application 110$_B$ to the host application 130 together with the first part of the access key K_1$_B$ associated with the second client user.

As an alternative to sending patient data D' directly in the message, the message may contain a link to the patient data D' or it may be in a file attached to the message.

In step 980: Identifying, using the host application 130, the second client user 121$_B$ based on the received first part of the access key K_1$_B$ associated with the second client user.

Identifying, the second client user 121$_B$ in step 980 may comprise:
generating a second part of the access key, based on the received first part K_1$_B$ of the access key associated with the second client user;
comparing the generated second part of the access key to one or more second parts of access keys stored in the memory accessible to the host application 130 to find a matching second part, wherein the stored one or more second parts of access keys have been generated during pairing of the host application 130 with one or more client applications 110; and
if a matching second part of an access key is found, identifying the second client user 121$_B$ as the client user associated with the matching second part stored in the memory.

As the second client user 121$_B$ is stored in the memory of the host application 130 along with information or in a format indicating that the second client user 121$_B$ is the intended recipient of the data comprised in the message, this identification step is also an authentication of the second client user 121$_B$ as being allowed access to the data comprised in the message.

In response to identifying the second client user 121$_B$, the method continues in step 990.

In step 990: Sending the stored medical data MD concerning the at least one patient and information identifying each of the at least one patient, from the host application 130 to the second client application 110$_B$.

In this respect, the method may comprise, using the host application 130, decrypting or in other ways rendering the medical data MD and/or patient identity information readable before sending them to the second client application 110$_B$, if any or both of them have previously been made unreadable. Thereby, the receiving party can review the content of the patient data D' using the unique access key K only if the both the sending party, herein the first client application, and the receiver application, herein the second client application, have each been paired with the host application according to embodiments presented herein.

In one or more embodiments, the client application 110 and/or the host application 130 may be configured to perform any or all of the relevant method steps and functions presented herein.

Further Embodiments

All of the process steps, as well as any sub-sequence of steps, described with reference to FIG. 2, 3, 4, 7 or 8 above may be controlled by means of a programmed processor. Moreover, although the embodiments of the invention described above with reference to the drawings comprise processor and processes performed in at least one processor, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

In some embodiments, there is provided a computer program loadable into a non-volatile data carrier communicatively connected to a processing unit, the computer program comprising software for executing the method according any of the method embodiments presented herein when the program is run on the processing unit. Where applicable, the computer program may comprise two separate parts, one part comprising software for executing the method steps performed by the at least one client application according to any of the method embodiments described herein, and one part comprising software for executing the method steps performed by the host application according any of the method embodiments presented herein, when the program is run on one or more processing unit In some embodiments, there is provided for each of the computer programs or parts of computer programs a non-volatile data carrier containing the computer program according to any of its embodiments.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A method in a healthcare monitoring system for anonymous communication of patient data associated with at least one patient from a host server, using a host application implemented in the host server, to an electronic user device, using a client application implemented in the electronic user device, via a wireless network, the method comprising:
    pairing the client application and the host application, wherein the pairing comprises:
        i) generating, using the host application, a unique access key for a client user using the client application, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client user;
        ii) storing the second part of the unique access key in a memory accessible by the host application, wherein the second part is stored in association with information identifying the client user;
        iii) sending the first part of the unique access key from the host application to the client application;
        iv) storing the first part of the unique access key in a memory accessible by the client application;
    sending, from the client application to the host application, a request to retrieve patient data from the host server, the request comprising a specification of the patient data to be retrieved and the first part of the access key;
    in response to receiving the request in the host application identifying, using the host application, the client user associated with the unique access key, by:
        i) generating a second part of the access key, based on the received first part of the access key;
        ii) comparing the generated second part of the access key to one or more second parts of access keys stored in the memory accessible to the host application to find a matching second part, wherein the stored one or more second parts of access keys have been generated during pairing of the host application with one or more client applications; and
        iii) if a matching second part of an access key is found, identifying the client user as the client user associated with the matching second part stored in the memory;
    checking, using the host application, if the identified client user is authorized to retrieve the requested patient data; and
    if the identified client user is authorized to retrieve the requested patient data, sending the requested patient data from the host application to the client application, wherein the patient data does not comprise any information identifying the at least one patient associated with the patient data.

2. The method of claim 1, wherein the method further comprises, prior to pairing the client application and the host application, authenticating the client user as an authorized user of the client application, using strong authentication.

3. The method of claim 1, wherein generating a unique access key for the client user comprises:
    generating, using the host application, a randomized numeric code that is unrelated to any information identifying the client user;
    receiving, in the client application, the randomized numeric code;
    sending a message in the form of a control signal from the client application to the host application in response to receiving the unique access key;
    receiving, in the host application, the control signal; and
    generating, in the host application, the unique access key in response to receiving the control signal.

4. A healthcare monitoring system for anonymous communication of patient data associated with at least one patient from a host server, using a host application implemented in the host server, to an electronic user device, using a client application implemented in the electronic user device, via a wireless network, wherein:
    the electronic user device comprises a client application;
    the host server comprises a host application;

the client application is configured to communicate with the host application via the wireless network;

the system further comprises a memory accessible by the client application, and a memory accessible by the host application;

wherein the system is configured to pair the client application and the host application, by:

the host application being configured to:
- i) generate a unique access key for the client user, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client user;
- ii) store the second part of the unique access key in the memory accessible by the host application, wherein the second part is stored in association with information identifying the client user; and
- iii) send the first part of the unique access key to the client application;

the client application being configured to:
- i) receive the first part of the unique access key from the host application; and
- ii) store the received first part of the unique access key in the memory accessible by the client application;

wherein the client application is further configured to:
send to the host application a request to retrieve patient data from the host server, the request comprising a specification of the patient data to be retrieved and the first part of the access key;

wherein the host application is further configured to, in response to receiving the request:
identify the client user associated with the unique access key, by:
- i) generating a second part of the access key, based on the received first part of the access key;
- ii) comparing the generated second part of the access key to one or more second parts of access keys stored in the memory accessible to the host application to find a matching second part, wherein the stored one or more second parts of access keys have been generated during pairing of the host application with one or more client applications; and
- iii) if a matching second part of an access key is found, identifying the client user as the client user associated with the matching second part stored in the memory;

check if the identified client user is authorized to retrieve the requested patient data; and if the identified client user is authorized to retrieve the requested patient data, send the requested patient data from the host application to the client application, wherein the patient data does not comprise any information identifying the at least one patient.

5. The healthcare monitoring system of claim 4, wherein the client application is configured to authenticate the client as an authorized user of the client application, using strong authentication, prior to the pairing of the client application and the host application.

6. The healthcare monitoring system of claim 4, wherein, in order to generate a unique access key for the client user:
the host application is configured to generate a randomized numeric code that is unrelated to any information identifying the client user;

the client application is configured to receive the randomized numeric code from the host application and send a message in the form of a control signal to the host application in response to receiving the unique access key; and the host application is configured to receive the control signal from the client application and generate the unique access key in response to receiving the control signal.

7. A method in a healthcare monitoring system for anonymous communication of patient data associated with a patient from an electronic user device, using a client application implemented in the electronic user device, to a host server, using a host application implemented in the host server, via a wireless network, and identification of the patient associated with the patient data after the patient data is received in the host server comprising:

pairing the client application and the host application, wherein the pairing comprises:
- i) generating, using the host application, a unique access key for a client user using the client application, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client user;
- ii) storing the second part of the unique access key in a memory accessible by the host application, wherein the second part is stored in association with information identifying the client user;
- iii) sending the first part of the unique access key from the host application to the client application;
- iv) storing the first part of the unique access key in a memory accessible by the client application;

sending patient data and the first part of the access key from the client application to the host application, wherein the patient data does not comprise any information identifying the patient;

receiving in the host application the patient data and the first part of the access key; and identifying, using the host application, the patient associated with the received patient data as the client user associated with the unique access key, by: generating a second part of the access key, based on the received first part of the access key;

comparing the generated second part of the access key to one or more second parts of access keys stored in the memory accessible to the host application to find a matching second part, wherein the stored one or more second parts of access keys have been generated during pairing of the host application with one or more client applications; and if a matching second part of an access key is found, identifying the patient as the client user associated with the matching second part stored in the memory.

8. The method of claim 7, wherein the method further comprises, prior to pairing the client application and the host application authenticating the client user as an authorized user of the client application, using strong authentication.

9. The method of claim 8, wherein authenticating the client user is performed using the client application.

10. The method of claim 7, further comprising storing the received patient data in the memory accessible to the client application.

11. The method of claim 7, wherein generating a unique access key for the client comprises:

generating, using the host application, a randomized numeric code that is unrelated to any information identifying the client;

receiving, in the client application, the randomized numeric code;

sending a message in the form of a control signal from the client application to the host application in response to receiving the unique access key;

receiving, in the host application, the control signal; and generating, in the host application, the unique access key in response to receiving the control signal.

12. A healthcare monitoring system for anonymous communication of patient data associated with a patient from an electronic user device to a host server, via a wireless network, and identification of the patient associated with the patient data after the patient data is received in the host server, wherein:

the electronic user device comprises a client application;

the host server comprises a host application;

the client application is configured to communicate with the host application via the wireless network;

the system further comprises a memory accessible by the client application, and a memory accessible by the host application;

wherein the system is configured to pair the client application and the host application, by:

the host application being configured to:

i) generate a unique access key for the client user, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client;

ii) store the second part of the unique access key in the memory accessible by the host application, wherein the second part is stored in association with information identifying the client user; and iii) send the first part of the unique access key to the client application; and the client application being configured to:

receive the first part of the unique access key from the host application; and store the received first part of the unique access key in the memory accessible by the client application;

the client application further being configured to send patient data and the first part of the access key to the host application, wherein the patient data does not comprise any information identifying the patient; and the host application further being configured to:

iv) receive patient data and the first part of the access key from the client application; and v) identify the patient associated with the received patient data as the client user associated with the unique access key, by:

generating a second part of the access key, based on the received first part of the access key;

comparing the generated second part of the access key to one or more second parts of access keys stored in the memory accessible to the host application to find a matching second part, wherein the stored one or more second parts of access keys have been generated during pairing of the host application with one or more client applications; and if a matching second part of an access key is found, identifying the patient as the client user associated with the matching second part stored in the memory.

13. The healthcare monitoring system of claim 12, wherein the host application is configured to authenticate a caregiver as an authorized user of the host application, using strong authentication, prior to the pairing of the client application and the host application.

14. The healthcare monitoring system of claim 12, wherein the client application is configured to authenticate a client user as an authorized user of the client application, using strong authentication, prior to the pairing of the client application and the host application.

15. The healthcare monitoring system of claim 12, wherein, in order to generate a unique access key for the client user:

the host application is configured to generate a randomized numeric code that is unrelated to any information identifying the patient;

the client application is configured to receive the randomized numeric code from the host application; and send a message in the form of a control signal to the host application in response to receiving the unique access key; and the host application is configured to receive the control signal from the client application; and generate the unique access key in response to receiving the control signal.

16. A method in a healthcare monitoring system for anonymous communication of patient data associated with a patient from an electronic user device, using a client application implemented in the electronic user device, to a host server, using a host application implemented in the host server, via a wireless network, and identification of the patient associated with the patient data after the patient data is received in the host server comprising:

pairing the client application and the host application, wherein the pairing comprises:

i) generating, using the host application, a unique access key for a client user using the client application, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client user;

ii) storing the second part of the unique access key in a memory accessible by the host application, wherein the second part is stored in association with information identifying the client user;

iii) sending the first part of the unique access key from the host application to the client application;

iv) storing the first part of the unique access key in a memory accessible by the client application;

sending information identifying the patient and the first part of the access key from the client application to the host application;

identifying, using the host application, the client user associated with the unique access key, by:

generating a second part of the access key, based on the received first part of the access key associated with the client user;

comparing the generated second part of the access key to one or more second parts of access keys stored in the memory accessible to the host application to find a matching second part, wherein the stored one or more second parts of access keys have been generated during pairing of the host application with one or more client applications; and if a matching second part of an access key is found, identifying the client user as the client user associated with the matching second part stored in the memory;

in response to identifying the client user:
  identifying, by the host application, the patient by mapping the received information identifying the patient to a list of patient identities stored in the memory of the host application; and
  sending an anonymous personal ID associated with the identified patient from the host application to the client application;

sending patient data from the client application to the host application, wherein the patient data comprises medical data concerning the patient and the anonymous personal ID for the patient, wherein neither the patient data nor the personal ID for the patient comprise any information identifying the patient;

receiving in the host application the patient data; and identifying, using the host application, the patient associated with the received patient data based on the received anonymous personal ID for the patient.

17. A healthcare monitoring system for anonymous communication of patient data associated with a patient from an electronic user device to a host server, via a wireless network, and identification of the patient associated with the patient data after the patient data is received in the host server, wherein:
  the electronic user device comprises a client application;
  the host server comprises a host application;
  the client application is configured to communicate with the host application via the wireless network;
  the system further comprises a memory accessible by the client application, and a memory accessible by the host application;
    wherein the system is configured to pair the client application and the host application, by:
    the host application being configured to:
    i) generate a unique access key for the client user, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client;
    ii) store the second part of the unique access key in the memory accessible by the host application, wherein the second part is stored in association with information identifying the client user; and
    iii) send the first part of the unique access key to the client application;
  the client application being configured to:
    iv) store the received first part of the unique access key in the memory accessible by the client application;
  wherein the client application is further configured to send information identifying the patient and the first part of the access key from the client application to the host application, wherein the host application is further configured to:
    identify the client user associated with the unique access key, by:
      generating a second part of the access key, based on the received first part of the access key associated with the client user;
      comparing the generated second part of the access key to one or more second parts of access keys stored in the memory accessible to the host application to find a matching second part, wherein the stored one or more second parts of access keys have been generated during pairing of the host application with one or more client applications; and
      if a matching second part of an access key is found, identifying the client user as the client user associated with the matching second part stored in the memory; and
    in response to identifying the client user:
      identify the patient by mapping the received information identifying the patient to a list of patient identities stored in the memory of the host application; and
      send an anonymous personal ID associated with the identified patient to the client application;
  wherein the client application is further configured to send patient data from the client application to the host application, wherein the patient data comprises medical data concerning the patient and the anonymous personal ID for the patient, wherein neither the patient data nor the personal ID for the patient comprise any information identifying the patient; and
  wherein the host application is further configured to receive the patient data and identify the patient associated with the received patient data based on the received anonymous personal ID for the patient.

18. A method in a healthcare monitoring system for anonymous communication of patient data associated with a patient from a first electronic user device, using a first client application implemented in the first electronic user device, to a second electronic user device, using a second client application implemented in the second electronic user device, via a wireless network, the method comprising:
  pairing each of the first and second client application with the host application, wherein each pairing comprises:
    i) generating, using the host application, a unique access key for a client user using the client application, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client user;
    ii) storing the second part of the unique access key in a memory accessible by the host application, wherein the second part is stored in association with information identifying the client user;
    iii) sending the first part of the unique access key from the host application to the client application;
    iv) storing the first part of the unique access key in a memory accessible by the client application;
  sending from the first client application to the host application the first part of the access key associated with the first client user, information identifying the second client user, medical data concerning the patient, and information identifying the patient;

identifying, using the host application, the first client user based on the received first part of the access key associated with the first client user;
in response to identifying the first client user:
identifying, by the host application, the patient by mapping the received information identifying the patient to a list of patient identities stored in the memory of the host application;
generating or retrieving from memory, using the host application, an anonymous personal ID stored in association with the identified patient;
storing, in the memory accessible to the host application, the information identifying the second client in association with the medical data;
sending patient data from the host application to the first client application, wherein the patient data comprises the medical data concerning the patient and the anonymous personal ID associated with the patient, wherein neither the medical data nor the anonymous personal ID comprises any information identifying the patient;
sending a message comprising the patient data from the first client application to the second client application;
in response to an input signal received in the second client application triggering opening of the message:
sending the message from the second client application to the host application together with the first part of the access key associated with the second client user; and
identifying, using the host application, the second client user based on the received first part of the access key associated with the second client user; and
in response to identifying the second client user, sending the stored medical data concerning the patient and information identifying the patient from the host application to the second client application.

19. The method of claim 18, wherein identifying, using the host application, the client user associated with the unique access key, comprises:
generating a second part of the access key, based on the received first part of the access key associated with the client user;
comparing the generated second part of the access key to one or more second parts of access keys stored in the memory accessible to the host application to find a matching second part, wherein the stored one or more second parts of access keys have been generated during pairing of the host application with one or more client applications; and
if a matching second part of an access key is found, identifying the client user as the client user associated with the matching second part stored in the memory.

20. A healthcare monitoring system for anonymous communication of patient data associated with a patient from a first electronic user device associated with a first client user to a second electronic user device associated with a second client user, via a wireless network, wherein:
the first electronic user device comprises a first client application and the second electronic user device comprises a second client application;
the system further comprises a host server comprising a host application;
each of the first and second client application is configured to communicate with the host application via the wireless network;
the system further comprises a respective memory accessible by each of the first and second client applications, and a memory accessible by the host application;
wherein the system is configured to pair each of the first and second client application with the host application, by:
the host application being configured to, for each of the first and second client user:
i) generate a unique access key for the client user, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the client user;
ii) store the second part of the unique access key in the memory accessible by the host application, wherein the second part is stored in association with information identifying the client user; and
iii) send the first part of the unique access key to the respective client application;
and each of the first and second client application being configured to:
iv) store the received first part of the unique access key in the memory accessible by the respective client application;
wherein the first client application is further configured to send to the host application the first part of the access key associated with the first client user, information identifying the second client user, medical data concerning the patient, and information identifying the patient;
wherein the host application is further configured to:
identify the first client user based on the received first part of the access key associated with the first client user;
identify the patient by mapping the received information identifying the patient to a list of patient identities stored in the memory of the host application;
store the information identifying the second client in association with the medical data; and
send patient data to the first client application, wherein the patient data comprises the medical data concerning the patient and an anonymous personal ID associated with the patient, wherein neither the medical data nor the anonymous personal ID comprises any information identifying the patient;
wherein the first client application is further configured to send to a message comprising the patient data to the second client application;
wherein the second client application is configured to, in response to an input signal received in the second client application triggering opening of the received message, send the message to the host application together with the first part of the access key associated with the second client user;
wherein the host application is configured to:
identify the second client user based on the received first part of the access key associated with the second client user; and
send the stored medical data concerning the patient and information identifying the patient to the second client application.

21. The system of claim 20, wherein the host application is configured to identify the client user associated with the unique access key by:

generating a second part of the access key, based on the received first part of the access key associated with the client user;

comparing the generated second part of the access key to one or more second parts of access keys stored in the memory accessible to the host application to find a matching second part, wherein the stored one or more second parts of access keys have been generated during pairing of the host application with one or more client applications; and if a matching second part of an access key is found, identifying the client user as the client user associated with the matching second part stored in the memory.

* * * * *